US007972302B2

United States Patent
Caizza et al.

(10) Patent No.: US 7,972,302 B2
(45) Date of Patent: *Jul. 5, 2011

(54) SYRINGE WITH DISABLING MECHANISM

(75) Inventors: Richard J. Caizza, Vernon, NJ (US); Robert Odell, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 167 days.

This patent is subject to a terminal disclaimer.

(21) Appl. No.: 12/137,732

(22) Filed: Jun. 12, 2008

(65) Prior Publication Data

US 2009/0048560 A1 Feb. 19, 2009

Related U.S. Application Data

(60) Provisional application No. 60/943,397, filed on Jun. 12, 2007.

(51) Int. Cl.
*A61M 5/00* (2006.01)
(52) U.S. Cl. ......................................................... 604/110
(58) Field of Classification Search .................... 604/110
See application file for complete search history.

(56) References Cited

U.S. PATENT DOCUMENTS

| 4,367,738 A | * | 1/1983 | Legendre et al. ............... 604/110 |
| 4,915,692 A | * | 4/1990 | Verlier ............................. 604/110 |
| 4,973,310 A | | 11/1990 | Kosinski |
| 5,047,017 A | | 9/1991 | Koska |
| 5,106,372 A | | 4/1992 | Ranford |
| 5,114,405 A | | 5/1992 | Winter |
| 5,116,320 A | | 5/1992 | Lo Duca |
| 5,188,616 A | * | 2/1993 | Nadal ............................ 604/218 |
| 5,269,760 A | | 12/1993 | Bina |
| 5,370,620 A | | 12/1994 | Shonfeld |
| 5,531,693 A | | 7/1996 | Vounatsos |
| 5,989,219 A | | 11/1999 | Villas et al. |
| 6,090,077 A | | 7/2000 | Shaw |
| 6,368,306 B1 | | 4/2002 | Koska |
| 6,599,269 B1 | | 7/2003 | Lewandowski et al. |
| 7,387,615 B2 | | 6/2008 | Coelho et al. |

(Continued)

FOREIGN PATENT DOCUMENTS

BE 1001579 A4 12/1989

(Continued)

OTHER PUBLICATIONS

PCT International Search Report and Written Opinion for PCT/US2008/082045, (May 6, 2009), 10 pgs.
"PCT International Search Report mailed Sep. 19, 2008 for International Application No. PCT/US2008/066655 filed Dec. 6, 2008," 7 pgs.

(Continued)

*Primary Examiner* — Nicholas D Lucchesi
*Assistant Examiner* — Jason Flick
(74) *Attorney, Agent, or Firm* — Jeanne P. Lukasavage; Diehl Servilla LLP

(57) ABSTRACT

Syringe assemblies having a passive disabling system to prevent reuse are provided. According to one or more embodiments, the syringe assembly comprises a barrel, plunger rod and stopper wherein the plunger rod further comprises a locking protrusion that locks the plunger rod within the barrel. Certain embodiments further include a frangible portion on the plunger rod that breaks when reuse is attempted. One or more embodiments include a plunger rod and stopper attachment that prevents disassembly of the syringe assembly prior to use. Syringe assemblies of one or more embodiments also include visual indicators or markers indicating whether a syringe assembly is used or the plunger rod is locked within the barrel.

42 Claims, 18 Drawing Sheets

U.S. PATENT DOCUMENTS

| | | |
|---|---|---|
| 2004/0176722 A1 | 9/2004 | Capes et al. |
| 2005/0027250 A1 | 2/2005 | Suresh et al. |
| 2006/0052748 A1 * | 3/2006 | Coelho et al. ............... 604/110 |
| 2006/0173411 A1 | 8/2006 | Barere |
| 2009/0131869 A1 | 5/2009 | Caizza et al. |

FOREIGN PATENT DOCUMENTS

| | | |
|---|---|---|
| EP | 0340899 | 11/1989 |
| EP | 001106194 | 6/2001 |
| EP | 1106194 | 6/2001 |
| FR | 2 686 517 | 7/1993 |
| FR | 2 689 765 | 10/1993 |
| GB | 2197792 | 6/1988 |
| WO | WO 90/03818 | 4/1990 |
| WO | WO 9003818 A1 * | 4/1990 |
| WO | WO-03/037411 | 5/2003 |
| WO | WO 2004/033008 | 4/2004 |
| WO | WO-2004/045683 | 6/2004 |
| WO | WO-2008/154616 | 12/2008 |

OTHER PUBLICATIONS

"PCT Written Opinion mailed Sep. 19, 2008 for International Application No. PCT/US2008/066655 filed Dec. 6, 2008," 6 pgs.

"PCT Search Report", PCT/US08/66705, (Jan. 30, 2009), 6 pgs.

"PCT Written Opinion", PCT/US08/66705, (Dec. 12, 2009), 8 pgs.

"Non-Final Office Action", U.S. Appl. No. 12/137,854, filed (Feb. 4, 2010), 13 pgs.

"Non-Final Office Action", U.S. Appl. No. 12/262836, filed (Feb. 4, 2010), 16 pgs.

"Non-Final Office Action", U.S. Appl. No. 12,137,854, filed Jul. 21, 2010, 29.

"Non-Final Office Action", U.S. Appl. No. 12/262,836, filed Jul. 22, 2010, 23.

"Final Office Action in U.S. Appl. No. 12/137,854, dated Dec. 22, 2010", 20 pgs.

"Final Office Action in U.S. Appl. No. 12/262,836, dated Dec. 27, 2010", 25 pgs.

* cited by examiner

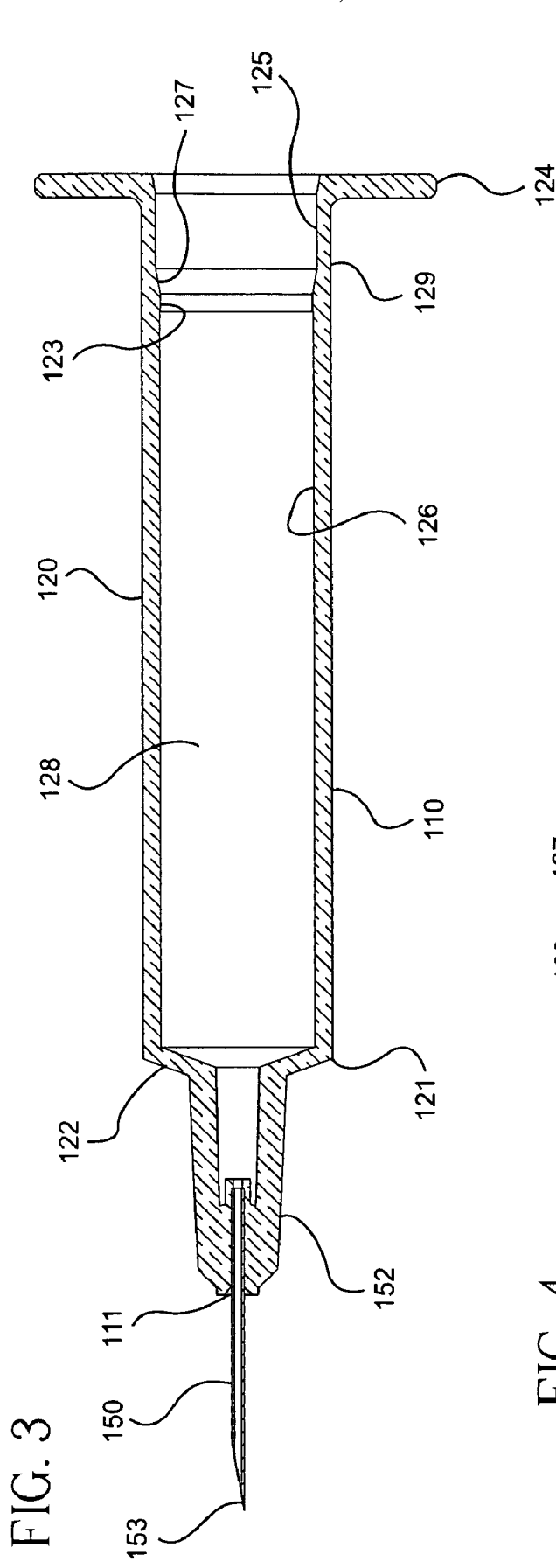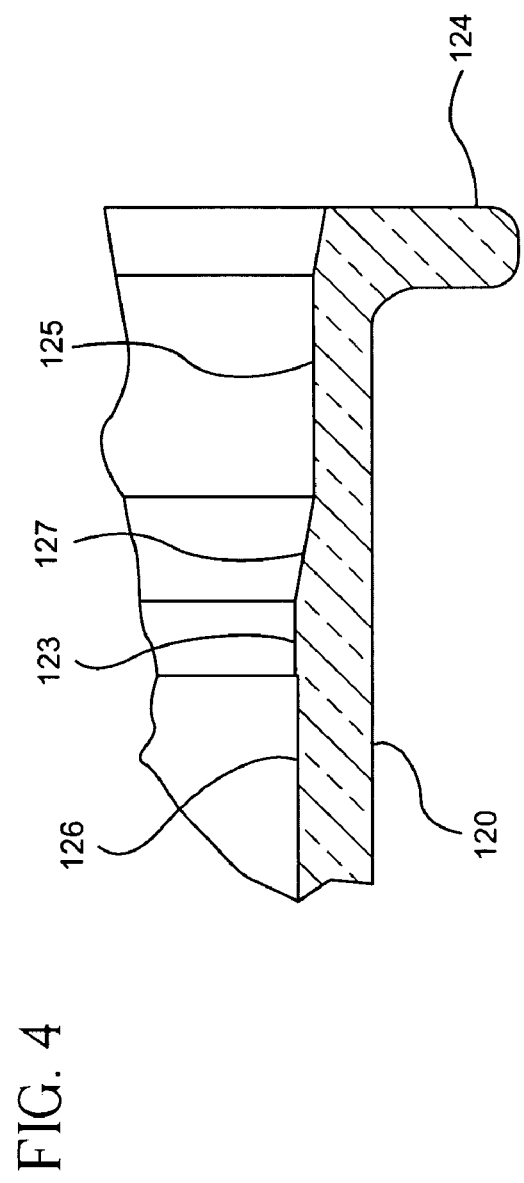
FIG. 3
FIG. 4

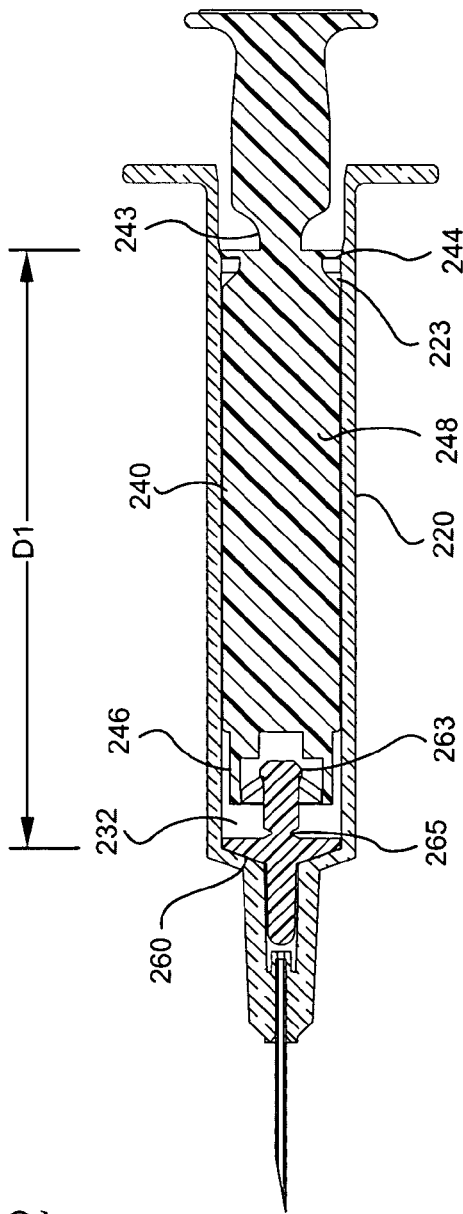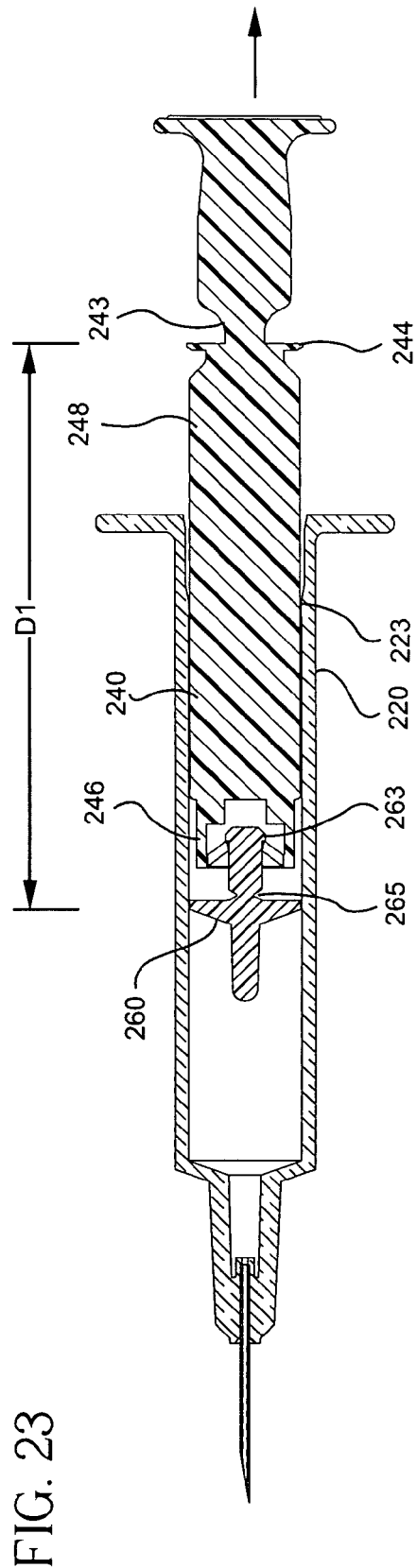
FIG. 22
FIG. 23

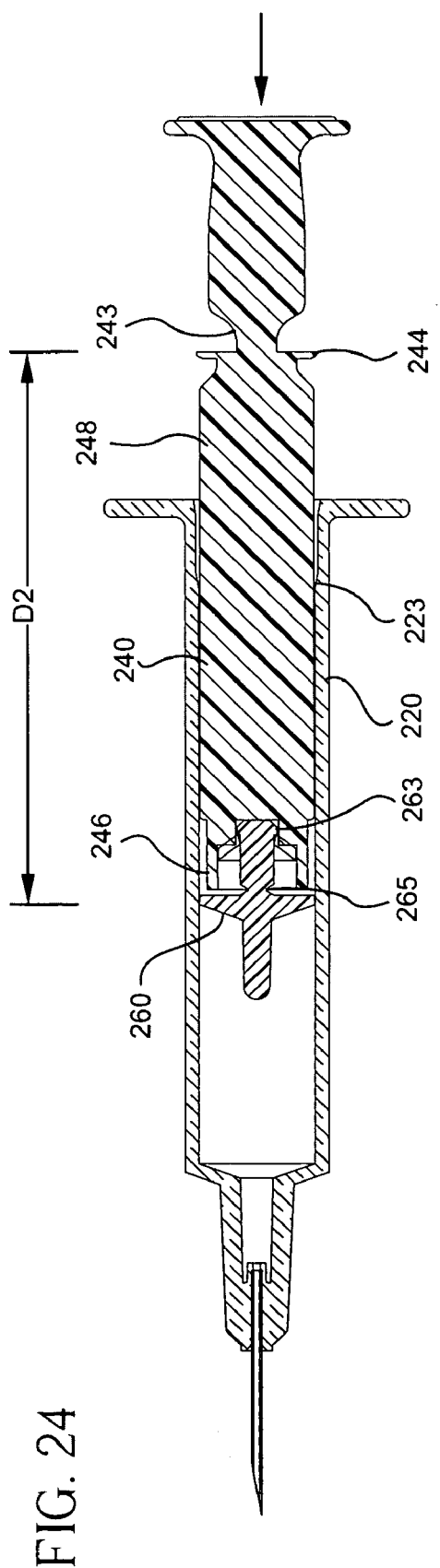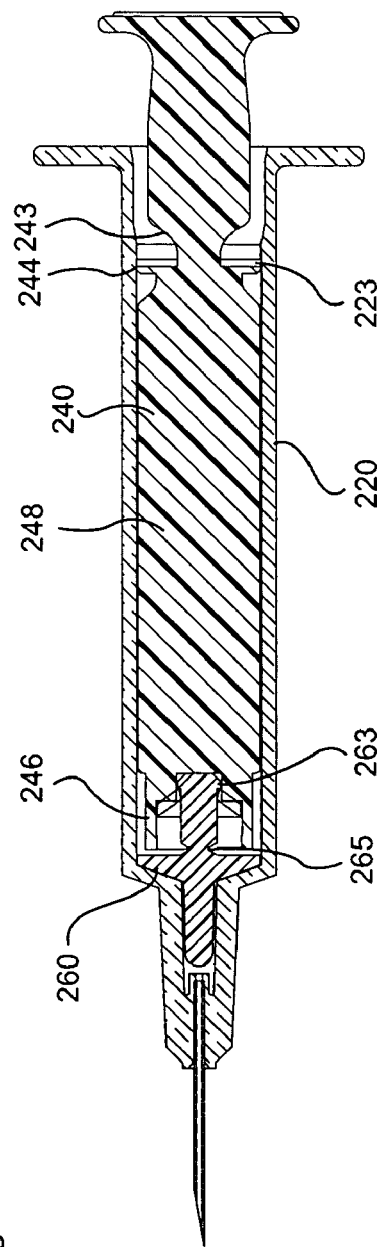
FIG. 24
FIG. 25

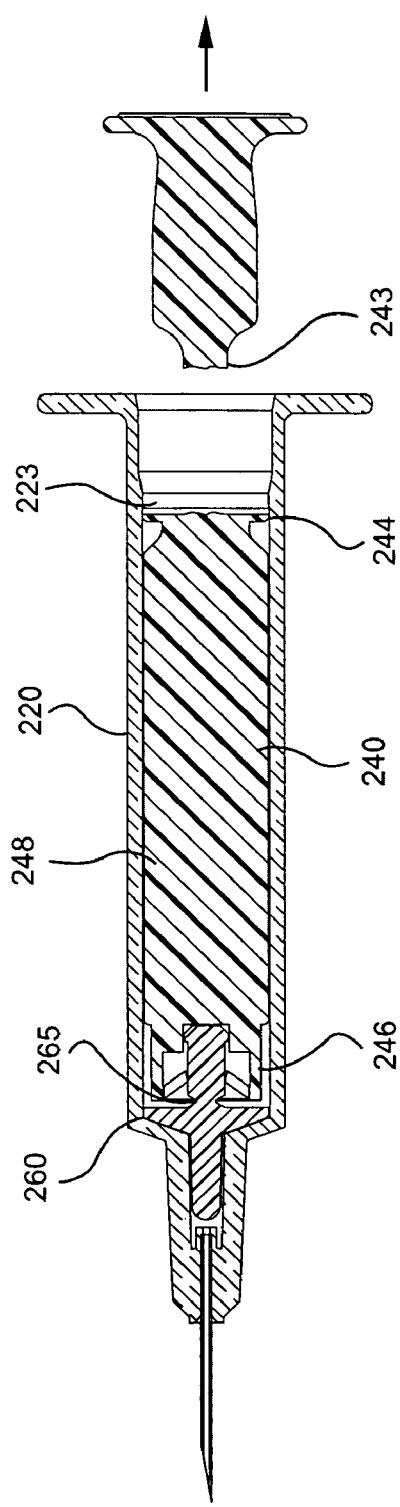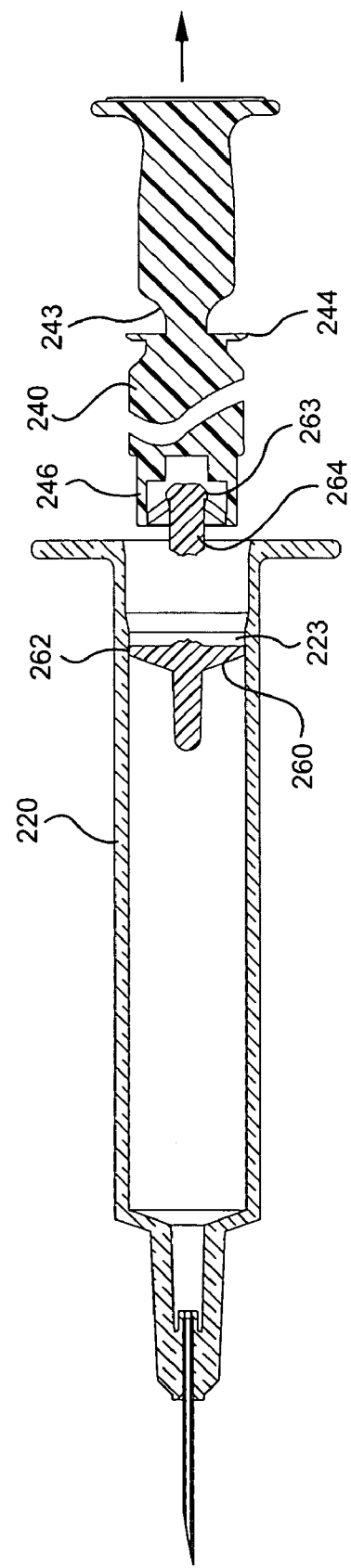

SYRINGE WITH DISABLING MECHANISM

CROSS-REFERENCE TO RELATED APPLICATIONS

This application claims the benefit of priority from U.S. Provisional Application No. 60/943,397, filed Jun. 12, 2007, the disclosure of which is hereby incorporated in its entirety by reference thereto.

TECHNICAL FIELD

Embodiments of the present invention relate to syringe assemblies having a passive locking mechanism which restricts distal movement of the plunger rod after injection to prevent reuse, syringe assemblies wherein the stopper and plunger rod operate using relative motion to passively disable the syringe, syringe assemblies including a removeably connected stopper and plunger rod to prevent disassembly of the syringe prior to use and syringe assemblies including visual indication or markings to indicate use of the syringe or a disabled syringe.

BACKGROUND

Reuse of hypodermic syringe products without sterilization or sufficient sterilization is believed to perpetuate drug abuse and facilitate the transfer of contagious diseases. The reuse of syringes by intravenous drug users further exacerbates the transfer of contagious diseases because they comprise a high-risk group with respect to certain viruses such as the AIDS virus and hepatitis. A high risk of contamination also exists in countries with shortages of medical personnel and supplies.

A syringe which can be rendered inoperable after use presents a viable solution to these issues. Various syringes have been proposed and are commercially available that can be disabled by the user by taking active steps to disable the syringe. Single-use syringes that do not require the user to actively disable the syringe are also thought to offer a solution. It would be desirable to provide syringes that are automatically or passively disabled from reuse and can be manufactured in a cost-effective manner by, for example, utilizing fewer parts. Further, markings or other indicators which visually indicate whether a syringe has been used or is disabled would also be desirable.

SUMMARY

A passive disabling system for a syringe assembly that activates after completion of an injection cycle is provided. A syringe assembly incorporates a stopper and plunger rod attached in a manner to prevent users from disassembling the syringe prior to completion of the injection cycle. In one or more embodiments of the invention, a user can fill, inject and/or reconstitute medication.

In this disclosure, a convention is followed wherein the distal end of the device is the end closest to a patient and the proximal end of the device is the end away from the patient and closest to a practitioner.

A syringe assembly is provided which includes a barrel, an elongate plunger rod and stopper having respective structures and assembly which allow the user to passively lock the plunger rod within the barrel to prevent reuse of the syringe assembly. The barrel includes a distal end, an open proximal end, a cylindrical sidewall, which defines a chamber in which fluid may be held, and a distal wall. An opening in the distal wall permits fluid to flow from the chamber through the opening. In one embodiment, the barrel includes a marker or indicator which indicates whether the syringe has been disabled or the plunger has been locked within the barrel.

In one or more embodiments, the sidewall of the barrel has a continuous diameter or first inner diameter. As used throughout this application, the term "diameter" is a measurement of the longest distance between the walls of the barrel having any cross-sectional shape. However, it will be appreciated that conventional syringes are typically cylindrical with a circular cross-sectional shape. In accordance with some embodiments of the present invention, the barrel includes a rib, locking rib or other such impediment suitable for restricting the proximal movement of the plunger rod, adjacent to its proximal end. In one embodiment, the rib has a second inner diameter, wherein the second diameter is less than the first diameter. One or more embodiments of the present invention include an increased diameter region located proximally from the rib having a third inner diameter, wherein the third diameter is greater than the first diameter and second diameter. A diameter transition region having an axial length located between the rib and the increased diameter region may be included. The diameter transition region can have a varying inner diameter, which increases in the proximal direction.

Embodiments of the present invention also include an extended plunger rod which has a proximal end, a distal end, and a main body between the proximal and distal end. In some embodiments, the plunger rod slides or otherwise moves proximally and distally within the chamber of the barrel.

The distal end of the plunger can include a stopper-engaging portion having a distal and proximal end. The stopper-engaging portion provides a means for the stopper and plunger rod to move proximally and distally within the barrel. The stopper-engaging portion allows the stopper and plunger rod to move proximally and distally relative to each other. In a specific embodiment, the stopper-engaging portion may include a rim at its distal end, or a retainer or alternate means suitable for restraining the stopper.

The stopper-engaging portion according to one or more embodiments may also include a visual indicator or a visual display that indicates use of the syringe or whether the syringe is disabled.

The plunger rod can further include means for locking the plunger rod in the barrel to prevent reuse of the syringe assembly when the syringe is fully injected or "bottomed." The means can have an outer diameter greater than the inner diameter of the barrel at the rib or the second inner diameter. As used herein, the term "bottomed" shall refer to the position of the syringe assembly wherein the stopper, while attached to the plunger rod, is in contact with the distal wall of the barrel and the plunger rod can no longer move in the distal direction.

One or more embodiments of the present invention utilize a protrusion, or annular protrusion that extends radially from the plunger rod. In some embodiments, the protrusion is located between the thumb press and the main body, as an example of a means for locking the plunger rod in the barrel. According to an embodiment of the invention, the protrusion is integrally molded to the plunger rod.

In one configuration, the protrusion has an outer diameter greater than the second inner diameter. Once the protrusion distally moves through the diameter transition region, past the rib and into the barrel, it becomes locked by the rib, thereby preventing proximal movement of the plunger rod. The protrusion of one embodiment is tapered or otherwise shaped in such a manner such that it may move in the distal direction past the rib more easily.

The plunger rod can further comprise at least one frangible portion for separating a portion of the plunger rod from the body. In this configuration, when a user attempts to reuse the syringe assembly or otherwise pull the plunger in the proximal direction out of the barrel, after the plunger rod has been locked, the plunger rod breaks at the frangible portion, leaving a portion of the plunger rod locked within the barrel. In a specific embodiment, the frangible portion is located between the protrusion and the thumb press.

The stopper has a proximal end and a distal end and the stopper is attached the stopper-engaging portion of the plunger rod. In some embodiments, the stopper moves distally and proximally within the barrel. The stopper also moves distally and proximally along a pre-selected axial distance relative to the stopper-engaging portion of the plunger rod, thereby allowing the protrusion to move distally past the rib into the locked position, when the syringe assembly is bottomed.

The stopper may further comprise a stopper body or stopper boss at the proximal end of the stopper. A peripheral lip may be included at the proximal end of the stopper body. A frangible connection may be provided to connect the stopper to the plunger rod, which may connect the stopper and the peripheral lip.

The stopper-engaging portion of the plunger rod and the stopper may be connected in a manner such that when the user applies a force in the proximal direction for aspiration or filling the syringe, the stopper remains stationary until plunger rod moves in the proximal direction the length of the pre-selected axial distance. In one embodiment, when a user continues to aspirate or fill the syringe assembly, the stopper begins to move in the proximal direction in tandem with the plunger rod, after the plunger rod has traveled the pre-selected axial distance in the proximal direction. An optional visual indicator or display disposed on the stopper-engaging portion of the plunger rod is visible when the user fills the syringe assembly.

In one or more embodiments of the present invention, when a user injects the contents of the syringe assembly, the attachment of the stopper and the stopper-engaging portion allow the plunger rod to move distally for a length of the pre-selected axial distance, while the stopper remains stationary. After the plunger rod travels distally for the length of the pre-selected axial distance, the stopper begins to move distally with the plunger rod. During such distal movement, where a visual indicator or display is utilized, the visual indicator or display disposed on the stopper-engaging portion of the plunger rod is no longer visible. Where a visual marker is utilized, the visual marker disposed on the barrel continues to be visible, even after the plunger rod is locked. As will be more fully described herein, the marker provides an alternative means of indicating the syringe has been disabled.

According to one embodiment of the present invention, the total length of the plunger rod is decreased by pre-selected axial distance when the stopper and plunger rod move together in the distal direction during injection of the contents of the syringe assembly. As such, the stopper and stopper-engaging portion of the syringe assembly are attached in a manner such that when a user has fully completed the injection cycle, the protrusion of the plunger rod advances past the rib of the barrel. In some embodiments, once the protrusion advances past the rib of the barrel, it locks the plunger rod within the barrel and prevents the user from reusing the syringe assembly or otherwise pulling the plunger rod out of the barrel. Once the plunger rod is locked within the barrel, the optional visual indicator or display on the stopper-engaging portion of the plunger rod is no longer visible, indicating the syringe has been disabled.

The syringe assembly may include one or more frangible portions of the plunger rod, which break when a user attempts to move the plunger rod in a proximal direction after the protrusion has advanced past the rib of the barrel. Other suitable means may be utilized for separating a portion of the plunger rod from the main body when the user applies sufficient proximal force to the plunger rod or otherwise attempts to reuse the syringe assembly after it is bottomed.

In accordance with one embodiment of the invention, the stopper and the stopper-engaging portion are attached in such a manner such that when a user attempts to disassemble the syringe assembly prior to aspiration, injection or bottoming, the stopper-engaging portion disengages from the stopper, leaving the stopper inside the barrel and allowing the separated plunger rod to be removed. In some embodiments, inner diameter of the barrel at the rib, or the second inner diameter, is less than the outer diameter of the stopper, and thereby prevents the stopper from moving proximally past the rib and causes the stopper-engaging portion to detach from the stopper, leaving the stopper inside the barrel. An optional frangible connection of the stopper breaks when a user attempts to disassemble the syringe assembly by applying a continuous force in the proximal direction to the plunger rod prior to aspiration, injection or bottoming.

BRIEF DESCRIPTION OF THE DRAWINGS

FIG. 3 shows a cross-sectional view of the barrel shown in FIG. 2 taken along line 3-3;

FIG. 4 is an enlarged view of a portion of the barrel shown in FIG. 3;

FIG. 22 is a cross-sectional view taken along line 22-22 of the syringe assembly shown in FIG. 19;

FIG. 23 is an illustration of FIG. 22 showing the plunger rod being moved in the proximal direction;

FIG. 24 is an illustration of FIG. 23 showing the plunger rod being moved in the distal direction;

FIG. 25 is an illustration of FIG. 24 showing the plunger rod in a locked position in the syringe barrel;

FIG. 26 is an illustration of FIG. 25 showing a proximal portion of the plunger rod being broken from the syringe assembly after the plunger rod has been locked in the barrel; and FIG. 27 is an illustration of FIG. 22 showing the plunger rod being moved in the proximal direction and the stopper disengaging from the plunger rod.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Figure 1:
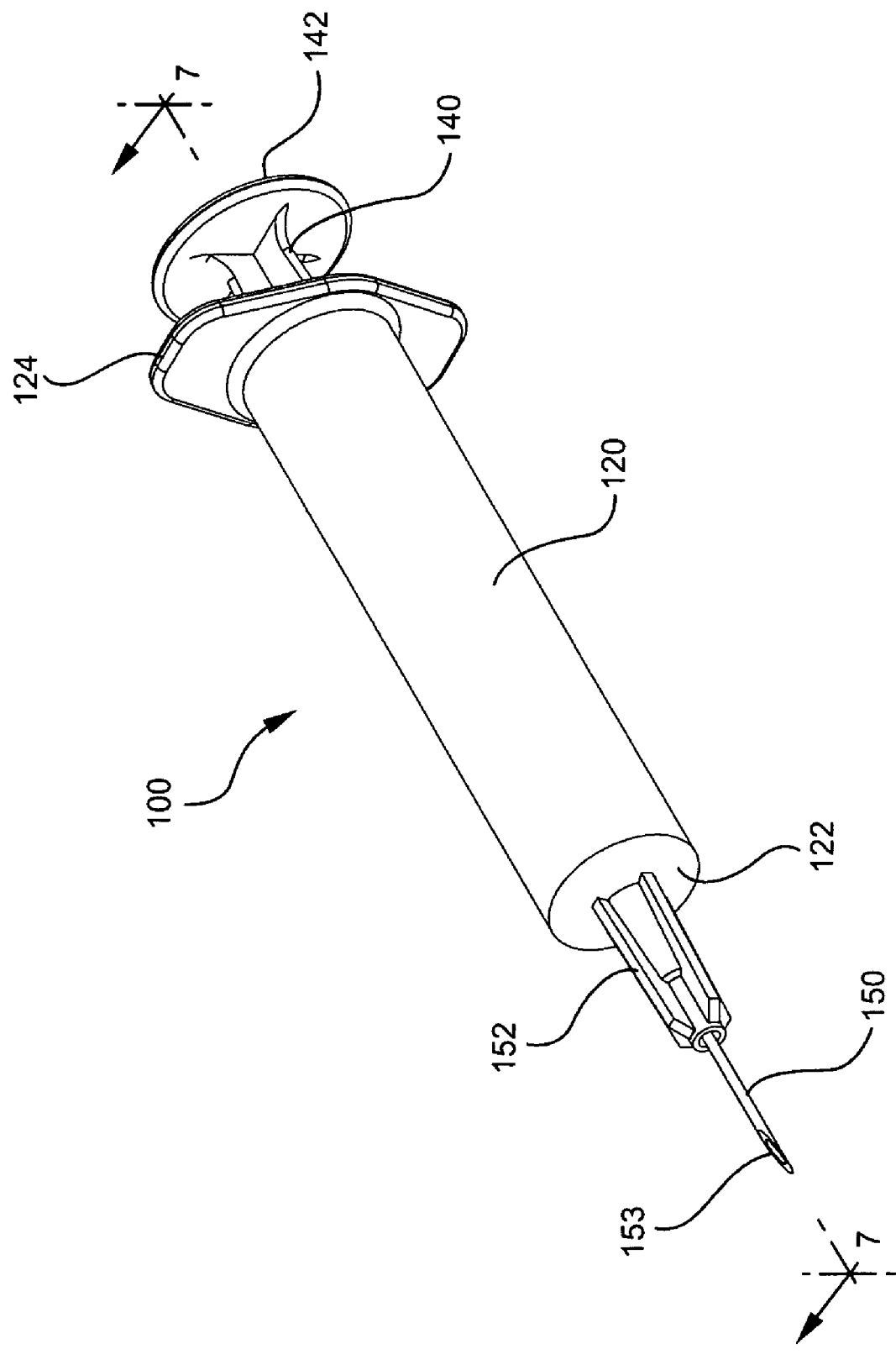
FIG. 1 illustrates a perspective view of a syringe assembly according to an embodiment of the invention shown.
Figure 2:
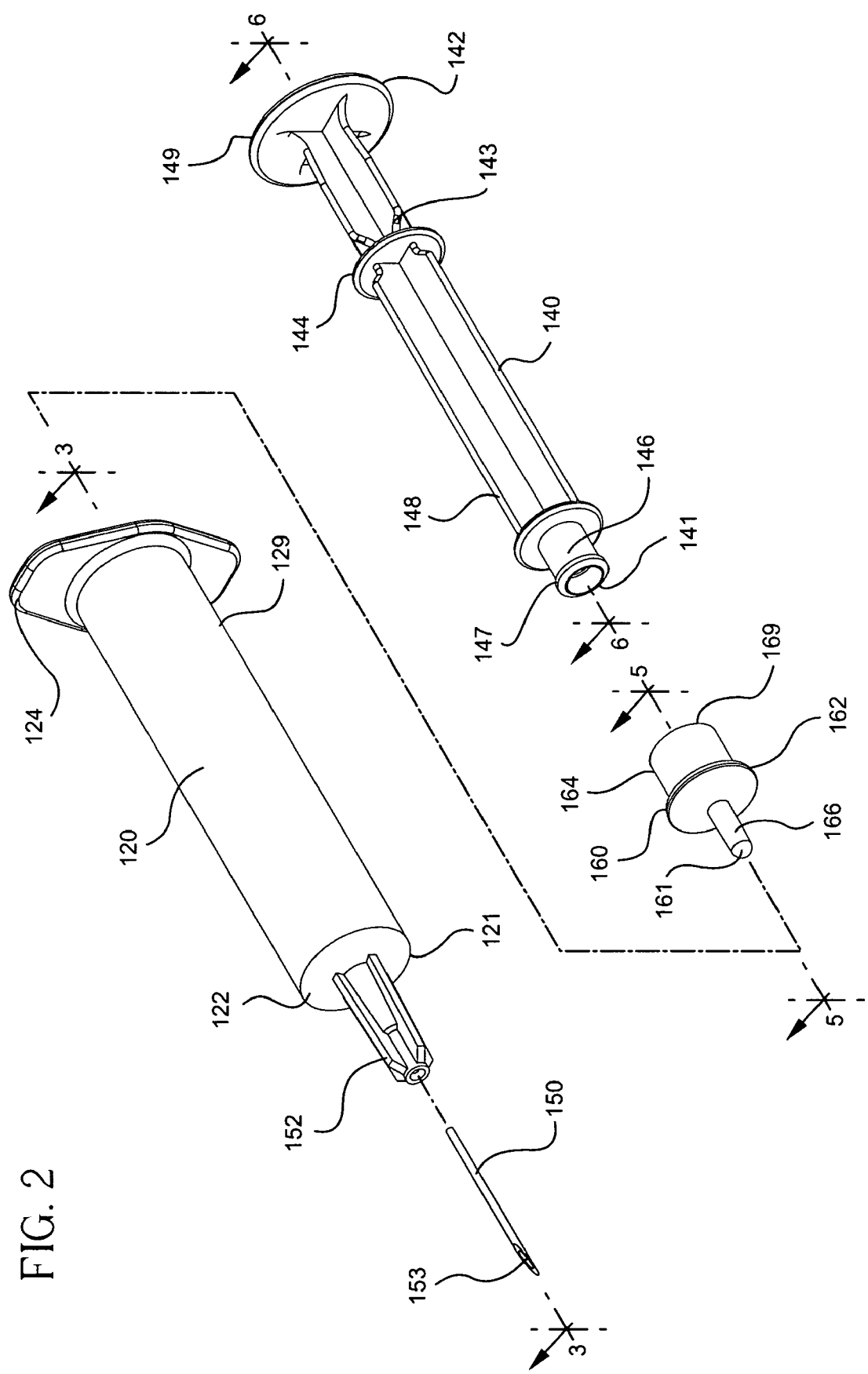
FIG. 2 illustrates a disassembled perspective view of a syringe assembly according to an embodiment of the invention.

One aspect of the present invention provides for a syringe assembly including a barrel, plunger rod and stopper having individual features and construction which allow the user to passively lock the plunger rod within the barrel to prevent reuse of the syringe assembly. FIG. 1 shows a syringe assembly 100 according to one or more embodiments. As shown in FIG. 2, the syringe assembly includes a barrel 120, a plunger rod 140 and a stopper 160, arranged such that the proximal end 169 of stopper is attached to the distal end 141 of the plunger rod. The connected stopper 160 and plunger rod 140 are inserted into the proximal end 129 of the barrel 120.

As best shown in the FIG. 3, the barrel 120 has a cylindrical sidewall 110 with an interior surface 126 that defines a chamber 128. In one embodiment, the chamber 128 holds the contents of the syringe assembly which may include medication in powdered or fluid form. The barrel 120 is shown as having an open proximal end 129, a distal end 121, and a distal wall 122. The distal wall 122 has an opening 111 in fluid communication with the chamber 128.

The sidewall 110 of the barrel 120 defines a chamber having a continuous inner diameter along the longitudinal axis of the syringe. Alternatively, the barrel can include a sidewall has an inner diameter, which decreases linearly from the proximal end to the distal end. It is to be understood that the configuration shown is merely exemplary, and the components can be different in shape and size than shown. For example, the barrel can have an exterior prism shape, while retaining a cylindrical interior shape. Alternatively, both the exterior and interior surfaces of the barrel can have non-circular cross-sectional shapes.

The syringe barrel 120 is shown as having a peripheral flange 124 attached at the proximal end 129 of the barrel 120. The barrel 120 further includes a needle cannula 150, having a lumen 153 attached to the opening 111 in the distal wall 122 of the barrel 120. As is known in the art, attachment means 152 is provided for attaching the needle cannula 150 to the distal wall 122. The assembly 100 may also include a protective cap over the needle cannula (not shown).

As shown more clearly in FIG. 4, the barrel 120 further includes a rib 123 adjacent its proximal end 129. The inner diameter of the barrel at the location of the rib 123 is smaller than the inner diameter of the barrel 120 at other locations along the length of the barrel. One or more optional tabs or detents can be used to create a region of the barrel having a diameter smaller than the inner diameter of the barrel 120. In a specific embodiment, the rib can include a ring formed along entire circumference of the interior surface 126 or a portion of the interior surface 126 of the inner diameter of the barrel 120 (not shown). The barrel 120 also includes a diameter transition region 127 adjacent to the rib 123 at the proximal end 129 of the barrel 120. The inner diameter of the barrel at the diameter transition region 127 increases from the distal end 121 to the proximal end 129 of the barrel 120. In the embodiment shown, the barrel includes an increased diameter region 125 adjacent to the diameter transition region at the proximal end 129 of the barrel. The inner diameter of the barrel 120 at the increased diameter region 125 is greater than the inner diameter of the barrel of the entire diameter transition region 127.

The barrel may be made of plastic, glass or other suitable material. The barrel further includes optional dosage measurement indicia (not shown).

Figure 5:
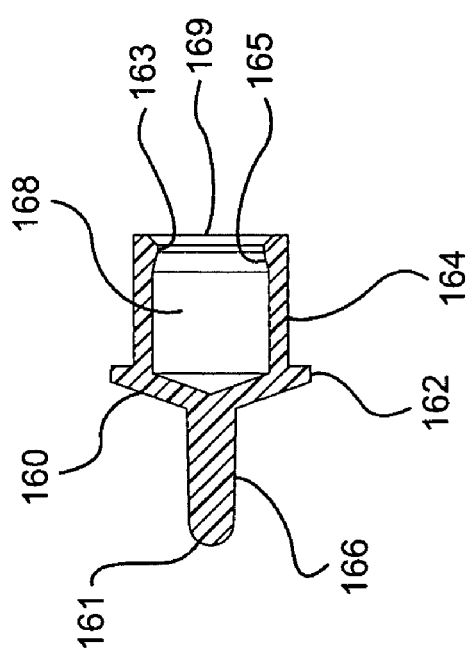
FIG. 5 is a cross-sectional view of the stopper shown in FIG. 2 taken along line 5-5.

Referring now to FIG. 5, the stopper 160 has a distal end 161, a proximal end 169, a stopper body 164 and a peripheral edge 162 which forms a seal with the interior surface 126 of the barrel. In one or more embodiments, the peripheral edge 162 of the stopper 160 has a larger diameter than the diameter of the interior surface of the rib 123. The stopper 160 shown in FIG. 5 includes an optional elongate tip 166 on its distal end 161 to facilitate reduction of the residual fluid and expulsion of fluid from the syringe barrel.

The stopper 160 is shown as further having a tapered portion 165 adjacent to the stopper body 164 at its proximal end 169. A neck 163 is adjacent to the tapered portion 165 at the proximal end 169 of the stopper 160. The stopper body 164 is shown as also including an interior recess 168, which allows the stopper-engaging portion 146 of the plunger rod 140 to connect to the stopper 160. A peripheral rim 147 may be provided to help retain the stopper 160 on the plunger rod 140. As with the rib of the barrel, detents or tabs can be used to retain the stopper 160 on the plunger rod 140.

The stopper is typically made of plastic or other easily disposable and/or recyclable material. It may be desirable to incorporate natural or synthetic rubber in the stopper or use a natural or synthetic rubber seal with the stopper. It will be understood that the stopper may incorporate multiple seals.

Figure 6:
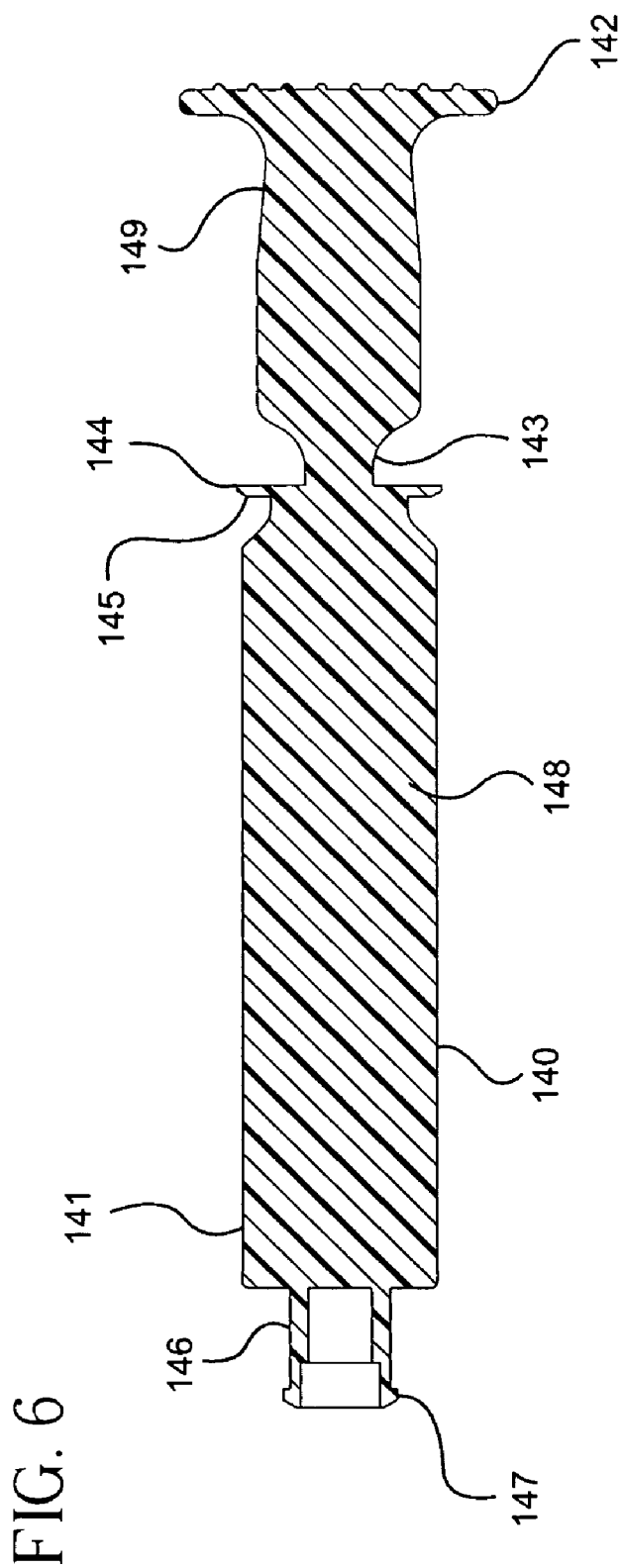
FIG. 6 is a cross-sectional view of the plunger rod shown in FIG. 2 taken along line 6-6.

Referring now to FIG. 6, the syringe assembly includes a plunger rod 140 having a proximal end 149, a distal end 141, and a main body 148 extending between the proximal end 149 and distal end 141. The plunger rod 140 further includes a thumb press 142 at the proximal end 149 of the plunger rod 140. In the embodiment shown, the thumb press 142 further includes a textured surface, writeable surface and/or label.

Still referring to FIG. 6, the plunger rod 140 further includes a protrusion 144 shown as an annular protrusion 144 between the thumb press 142 and the main body 148. The outer diameter of the plunger rod at the protrusion 144 is greater than the inner diameter of the barrel 120 at the rib 123. In some embodiments of the invention, the protrusion 144 includes a tapered portion 145 that facilitates distal movement of the protrusion past the rib 123 and into the barrel 120, as will become apparent in the subsequent discussion of operation of the syringe. In at least one embodiment, the syringe assembly is configured to allow the protrusion 144 to advance distally past the rib 123, to lock the plunger rod in the barrel when the user bottoms out the plunger rod in the barrel (as more clearly shown in FIGS. 10-11). In certain embodiments, the plunger rod 140 further includes at least one frangible connection or point 143 for separating at least a portion of the plunger rod from the main body when a user applies sufficient proximal force to the plunger rod after it has been locked. In the embodiment shown, the frangible point 143 is located between the protrusion 144 and the thumb press 142. It will be understood that the frangible connection or point 143 shown is exemplary, and other suitable means for permanently damaging the plunger rod or otherwise separating at least a portion of the plunger rod from the main body may be provided.

In the embodiment shown, the stopper 160 is permitted to move distally and proximally within the barrel when connected to the stopper-engaging portion 146 of the plunger rod 140. As will be understood better with the description of operation of the syringe assembly and with reference to FIG. 7, the stopper is capable of moving distally and proximally a pre-selected axial distance 132 relative to the stopper-engaging portion.

The plunger rod may be made of plastic or other suitable material. The protrusion may also be comprised of plastic or a harder material suitable for locking the plunger rod within the barrel.

Figure 7:
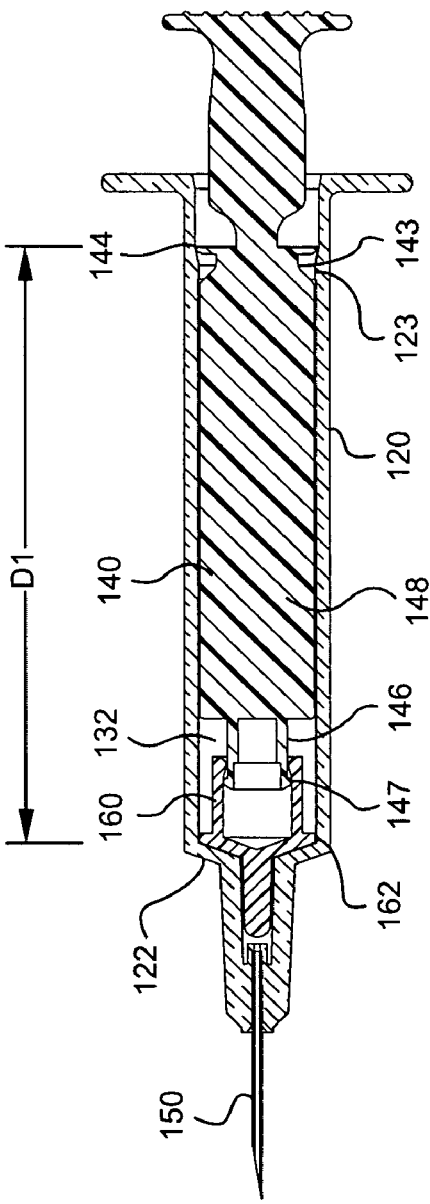
FIG. 7 is a cross-sectional view taken along line 7-7 of FIG. 1.

In FIG. 7, the barrel 120 holds the stopper 160 and plunger rod 140 in the chamber, wherein the stopper is bottomed, "parked" or is in contact with the distal wall 122 of the barrel 120. The peripheral edge of the stopper 162 forms a seal with the interior surface 126 of the barrel 120. In one embodiment, the stopper 160 is connected to the stopper-engaging portion 146 of the plunger rod 140. The stopper-engaging portion 146 is removeably held in the recess 168 of the stopper body 164 by the neck 163.

In FIG. 7, a gap between stopper 160 and the distal end of the main body 148 defines a pre-selected axial distance 132 prior to the injection cycle. In at least one embodiment, the protrusion 144 remains on the proximal side of the rib 123 because the length of the plunger rod 140 and stopper combined, along with the pre-selected axial distance 132, is greater than the length of the barrel 120 from the distal wall 122 to the proximal end of the barrel 120. The distance between the protrusion 144 and the peripheral edge 162 of the stopper body 164 defines a first distance, D1.

Figure 8:
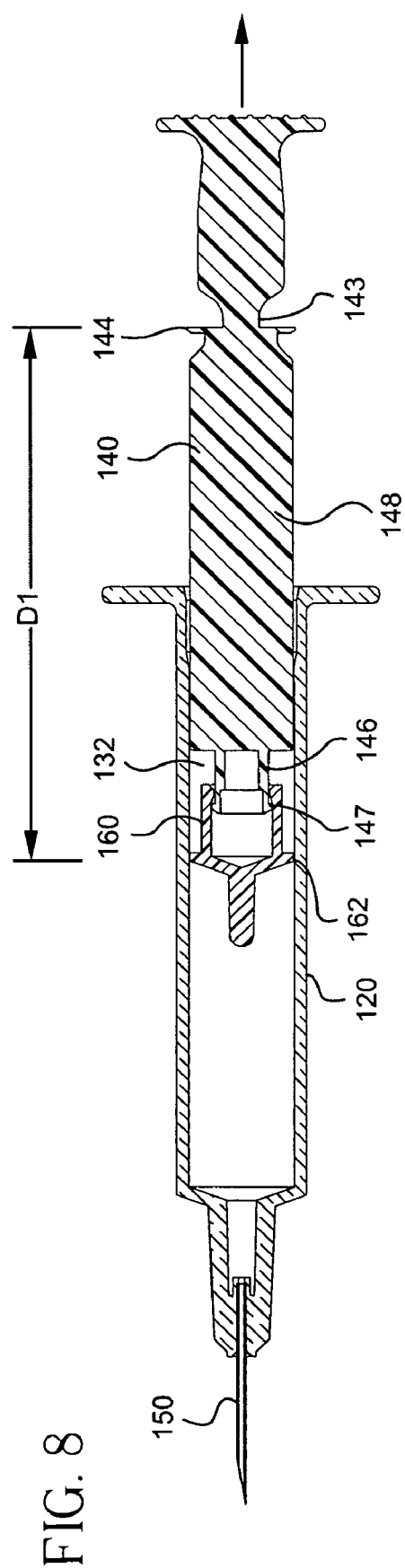
FIG. 8 is an illustration of FIG. 7 showing the plunger rod being moved in the proximal direction.

FIG. 8 illustrates the syringe assembly in use and specifically shows an aspiration or filling step, according to one or more embodiments of the present invention. When the user applies a force to the plunger rod 140 in the proximal direction shown by the arrow in FIG. 8, the plunger rod 140 and the stopper 160 move together in the proximal direction, while the stopper-engaging portion 146 is connected to the stopper 160 by the rim 147. In one or more embodiments, the gap defining the pre-selected axial distance 132 is maintained while the stopper 160 and plunger rod 140 move together in the proximal direction along the interior surface of the syringe barrel. The user terminates the application of proximal force on the plunger rod 140 once the desired amount of medicament is drawn into the syringe. During the aspiration step, the plunger rod and the stopper body move in the proximal direction together to draw medication into the syringe, while maintaining the first distance D1.

Figure 9:
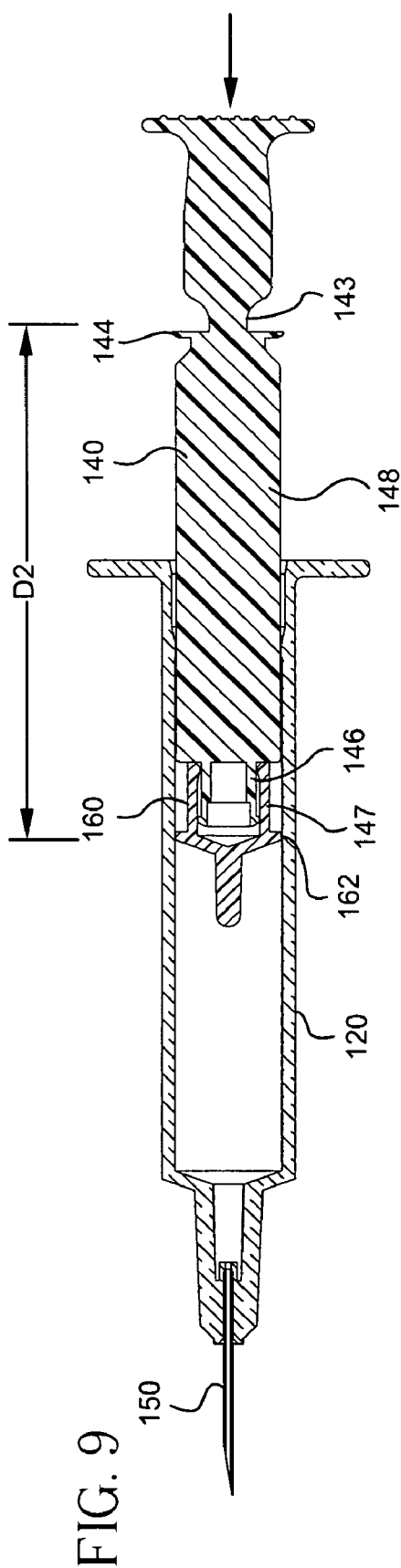
FIG. 9 is an illustration of FIG. 8 showing the plunger rod being moved in the distal direction.

FIG. 9 also shows the syringe assembly in use and specifically demonstrates application of distal force to the plunger rod during injection. In one embodiment, when the user applies a force in the distal direction to the plunger rod 140 as indicated by the arrow, the plunger rod 140 moves in a distal direction for the length of the gap defining the pre-selected axial distance 132 in FIG. 7, while the stopper 160 remains stationary. The stopper 160 remains stationary because the frictional force created by the peripheral edge 162 of the stopper on the interior surface 126 of the barrel is greater than the frictional force created by the stopper-engaging portion 146 entering the recess 168 of the stopper 160. Consistent with at least one embodiment, once the stopper-engaging portion has distally moved the length of the pre-selected axial distance 132 and is in contact with the proximal end of the recess 169, the stopper 160 and the plunger rod 140 begin to move in tandem in the distal direction. Further, the force applied by the user is greater than the friction between the peripheral edge 162 of the stopper 160 and the interior surface 126 of the barrel, and therefore the stopper 160 is forced to move in the distal direction with the plunger rod 140. In one embodiment, the user may inject a limited amount of the fluid aspirated or exert a limited force on the plunger rod in the distal direction to flush or expel some of the aspirated fluid, without locking the plunger rod, provided that the syringe assembly is not bottomed. However, as will be described further with respect to FIG. 10, a user may bottom the stopper against the distal wall of the syringe barrel, locking the plunger rod in the barrel.

When expelling the contents of the syringe, the plunger rod moves in a distal direction the length of the pre-selected axial distance 132 shown in FIG. 7 while the stopper body remains stationary, consequently closing the gap defining the pre-selected axial distance 132. After the contents of the syringe have been fully expelled, the distance between the protrusion 144 and the peripheral edge 162 defines a second distance, D2, wherein D2 is the difference between the first distance, D1, and the gap defining a pre-selected axial distance 132.

Figure 10:
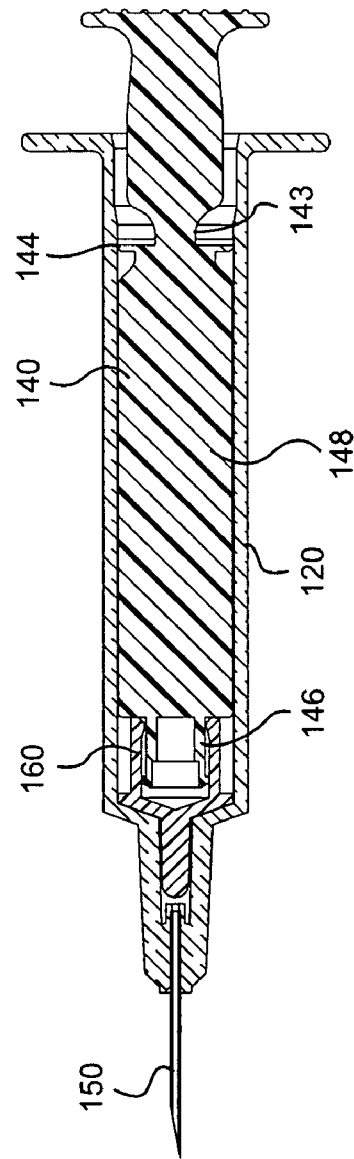
FIG. 10 is an illustration of FIG. 9 showing the plunger rod in a locked position in the syringe barrel.
Figure 11:
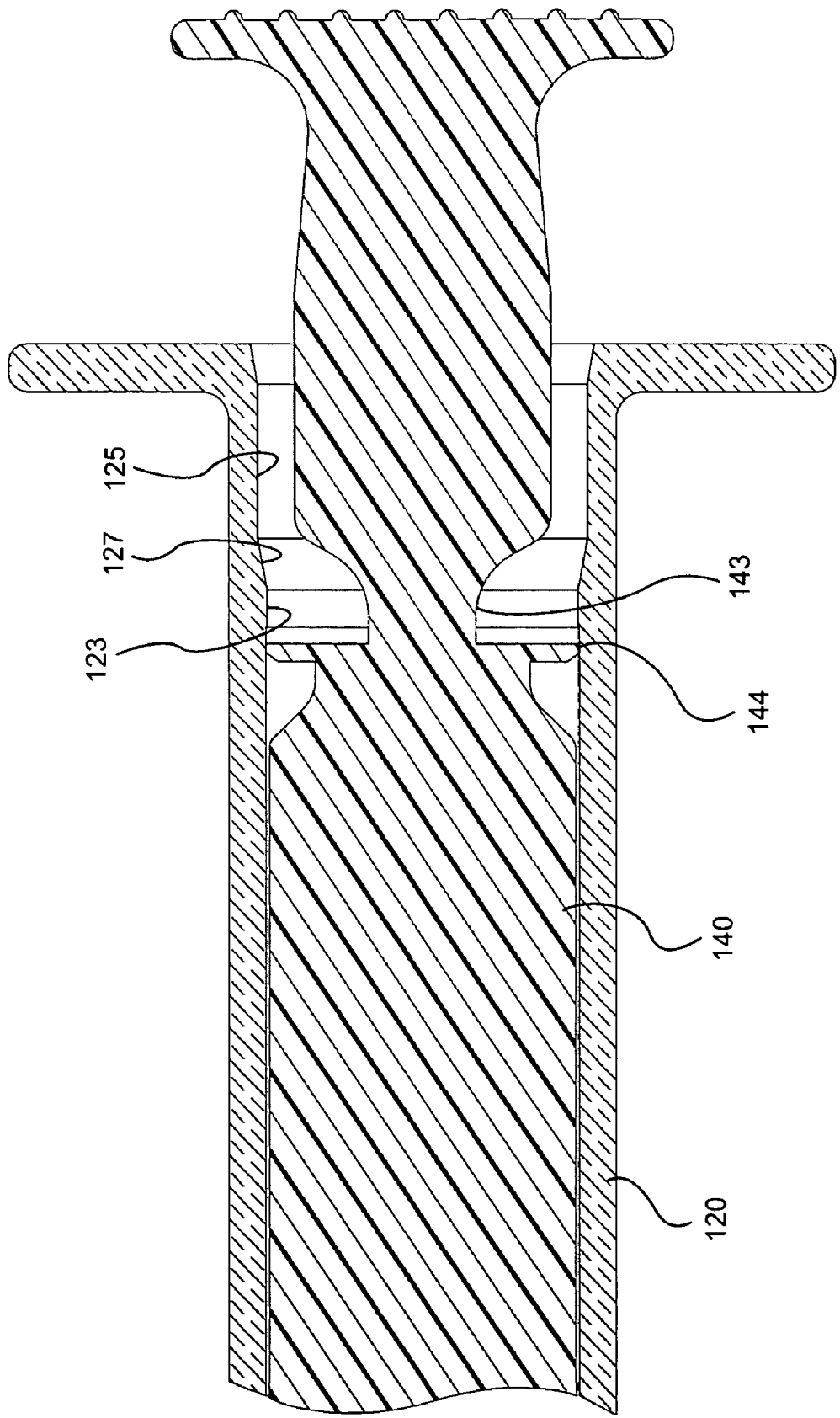
FIG. 11 is an enlarged view of a proximal portion of the assembly shown in FIG. 10.

FIG. 10 illustrates an embodiment of the syringe assembly after the plunger rod has been locked inside the barrel. In one or more embodiments, the entry of the stopper-engaging portion into the recess 168 of the stopper 160 (as also shown in FIG. 9) closes the gap defining the pre-selected axial distance 132, allowing the protrusion 144 to advance past the locking rib 123 (as more clearly shown in FIG. 11). The protrusion 144 has an outer diameter greater than the inner diameter of the barrel at the rib 123. Accordingly, in one or more embodiments, the rib 123 locks the protrusion 144 inside the barrel 120, and prevents proximal movement of the plunger rod 140.

Figure 12:
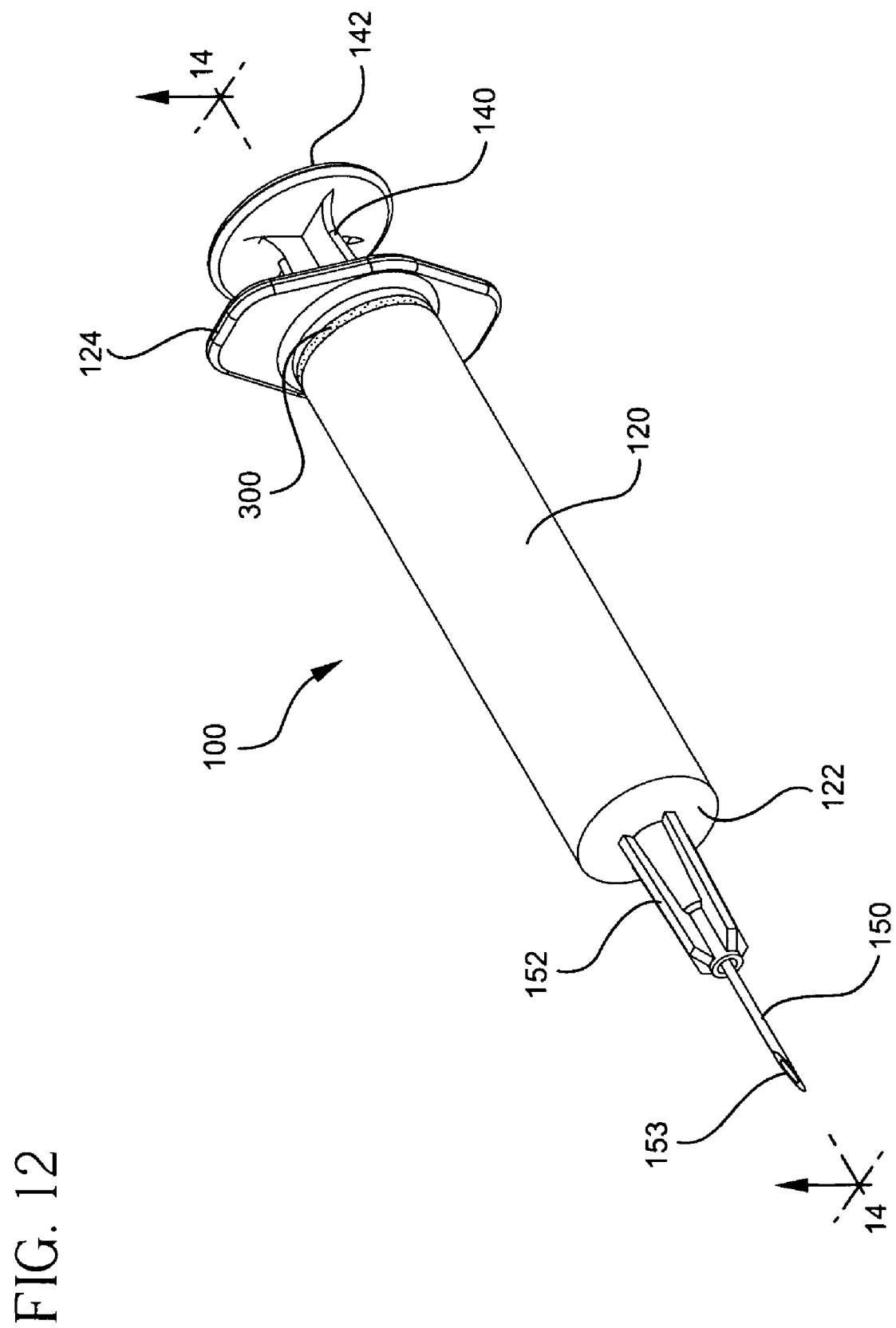
FIG. 12 illustrates a perspective view of an embodiment of a syringe assembly having a visual marker disposed on the barrel.

FIG. 12 shows a syringe assembly 100 in which the barrel 120 includes a visual marker 300. The marker is aligned with the rib 123, as more clearly shown in FIG. 16. The marker can be integrally formed on the sidewall of the barrel or can be added to the exterior surface of the sidewall. The marker can be printed in ink, adhesively applied, a textured surface or a separate piece that is fixed around the syringe barrel. The marker can form a ring around the circumference of the side wall or be in the form of tabs disposed at regular intervals around the circumference of the side wall. In a specific embodiment, the marker is a colored stripe. In a more specific embodiment, the marker can include text in the form of one or more letters and/or numbers, geometric shapes, symbols or combinations thereof to inform users the syringe is disabled.

Figure 13:
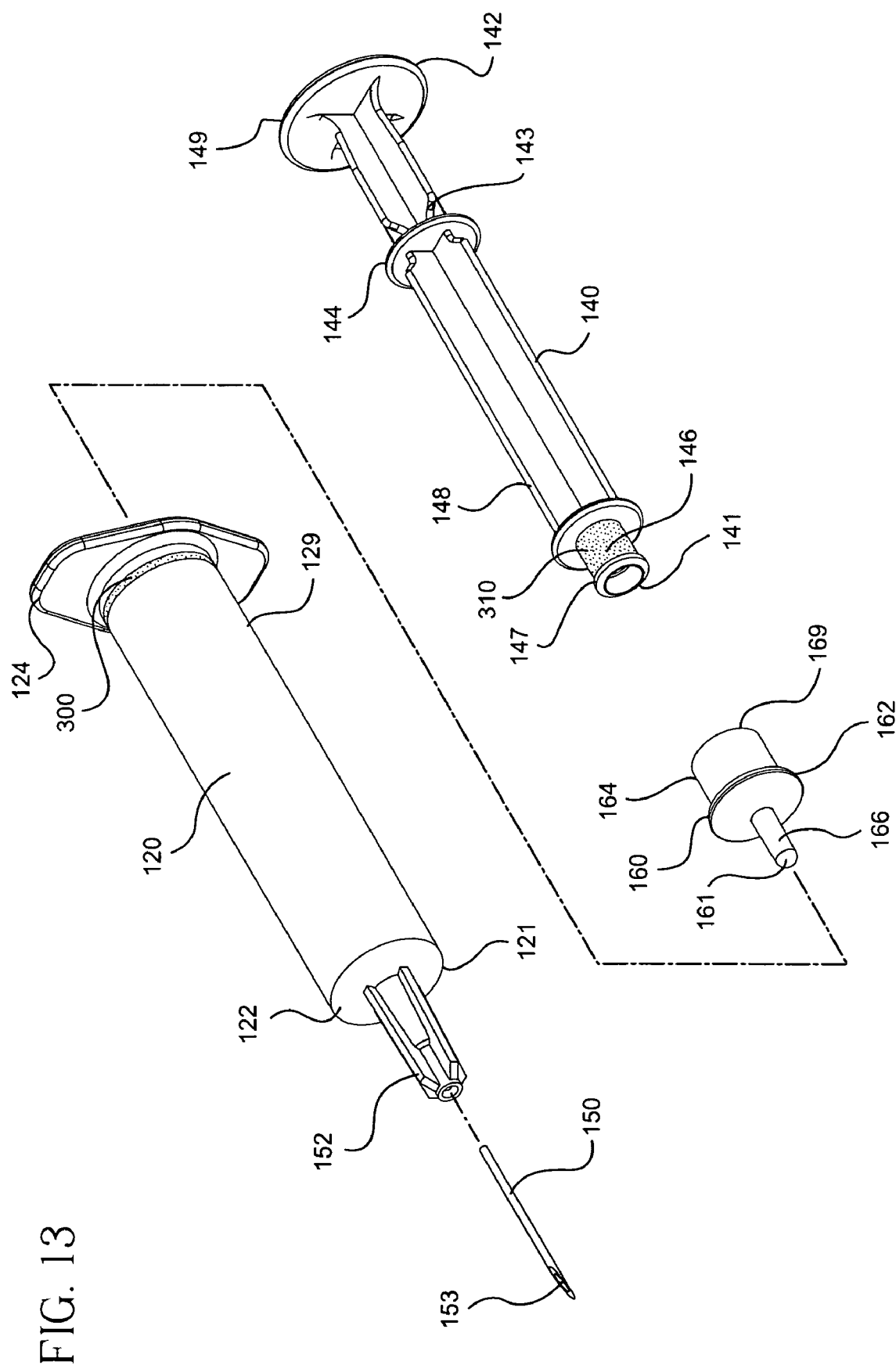
FIG. 13 illustrates a disassembled perspective view of an embodiment of a syringe assembly visual indicators or markers disposed on the barrel and the stopper-engaging portion of the plunger rod.

FIG. 13 shows a plunger rod 140 having a visual indicator or display 310 disposed on the stopper-engaging portion 146. As with the visual marker 300, the visual indicator 310 can be integrally formed with the stopper-engaging portion of the plunger rod or be added to the exterior surface thereof. The indicator or display can be printed in ink, adhesively applied, a textured surface or a separate piece that is fixed to the stopper engaging portion. In one or more embodiments, the indicator or display can comprise a pattern, a solid portion and or can cover the entire surface of the stopper-engaging portion. In a specific embodiment, the indicator is a colored stripe disposed along the length of the stopper-engaging portion 146 between the distal end 141 and the main body 148 of the plunger rod. In a more specific embodiment, the indicator is a colored stripe disposed along the circumference of the stopper-engaging portion 146 of the plunger rod. In an even more specific embodiment, the marker can include text in the form of one or more letters and/or numbers, geometric shapes, symbols or combinations thereof.

Figure 14:
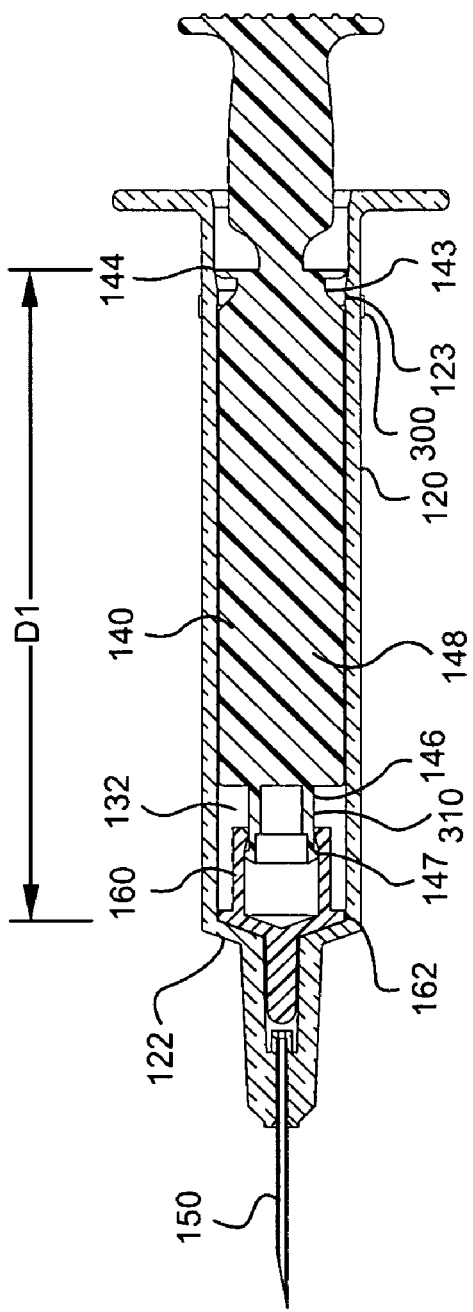
FIG. 14 is a cross-sectional view taken along line 14-14 of FIG. 12.

As more clearly shown in FIG. 14 a gap between stopper 160 and the distal end of the main body 148 defines a pre-selected axial distance 132 prior to the injection cycle. The visual indicator 310 is visible when the gap is present. The visual marker 300 is disposed on the exterior surface of the barrel 120 and aligned with the rib 123. As described with reference to FIG. 8, when the user applies a force to the plunger rod 140 in the proximal direction shown by the arrow in FIG. 8, the plunger rod 140 and the stopper 160 move together in the proximal direction, while the stopper-engaging portion 146 is connected to the stopper 160 by the rim 147. In one or more embodiments, the gap defining the pre-selected axial distance 132 is maintained while the stopper 160 and plunger rod 140 move together in the proximal direction along the interior surface of the syringe barrel. Accordingly, the visual indicator 310 continues to be visible.

As described with reference to FIG. 9, when expelling the contents of the syringe, the plunger rod moves in a distal direction the length of the pre-selected axial distance 132 shown in FIGS. 7 and 14 while the stopper body remains stationary, consequently closing the gap defining the pre-selected axial distance 132. The movement of the stopper-engaging portion, in the distal direction relative to the stopper allows the stopper-engaging portion 146 of the plunger rod to move into the recess 168 of the stopper (as shown in FIG. 9). As can be more clearly seen in FIG. 15, this relative movement allows the stopper body 164 covers the stopper-engaging portion and blocks visibility of the visual indicator 310.

Figure 15:
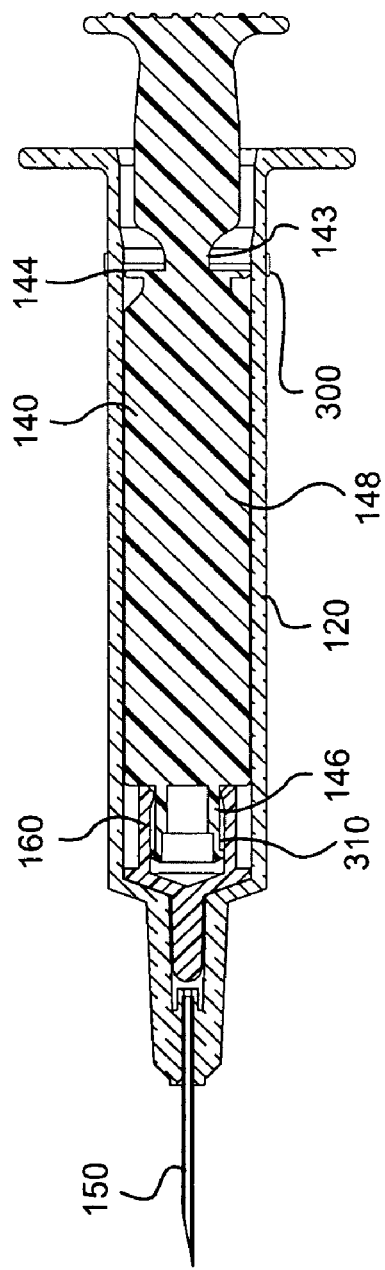
FIG. 15 is an illustration of FIG. 14 showing the plunger rod in a locked position in the syringe barrel.
Figure 16:
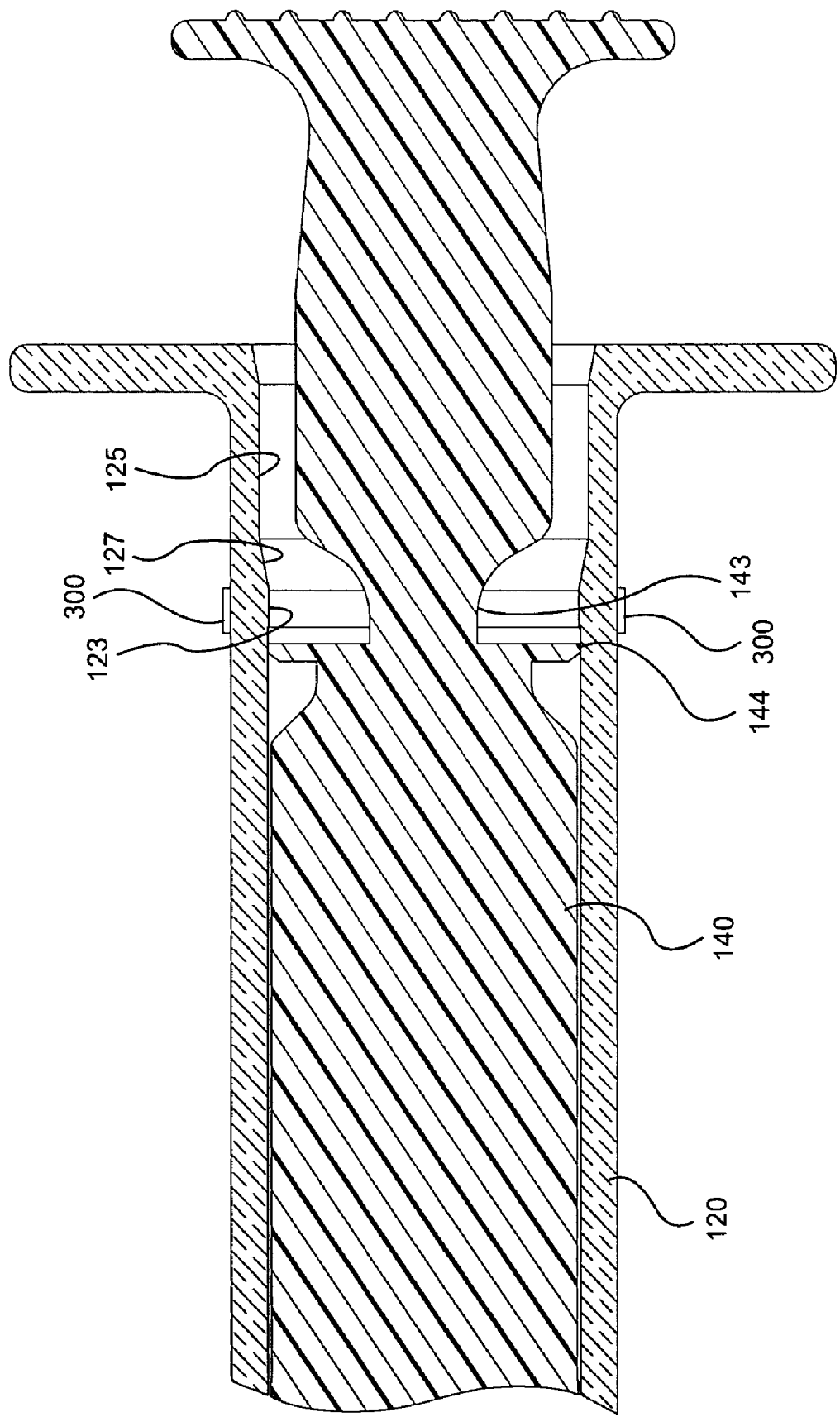
FIG. 16 is an enlarged view of a proximal portion of the assembly shown in FIG. 15.

As more clearly shown in FIGS. 15 and 16, the visual marker 300 disposed on the barrel 120 and aligned with the rib 123 also shows advancement of the protrusion 144 past the rib 123. In addition, the entry of the stopper-engaging portion into the recess 168 of the stopper 160 (as also shown in FIG. 9) also closes the gap defining the pre-selected axial distance 132, allowing the protrusion 144 to advance past the rib 123 (as more clearly shown in FIGS. 11 and 16). The location of the protrusion relative to the visual marker indicates whether the plunger rod has been locked within the barrel and the syringe assembly has been disabled. Before the plunger rod is locked, the protrusion 144 is proximally adjacent to the visual marker 300. Once the plunger rod is locked, the protrusion 144 is distally adjacent to the visual marker 300.

It will be appreciated that each of the visual marker 300 and the visual indicator 310 can be used alone or in combination.

Figure 17:
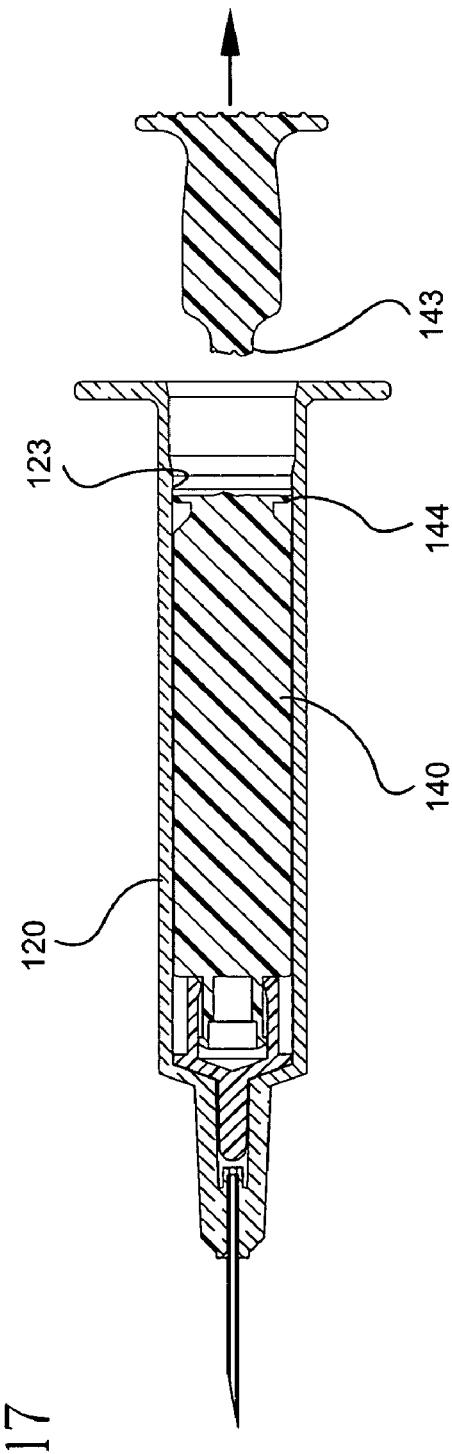
FIG. 17 is an illustration of FIG. 10 showing a proximal portion of the plunger rod being broken from the syringe assembly after the plunger rod has been locked in the syringe barrel.

FIG. 17 shows the assembly after the plunger rod 140 has been locked in the barrel 120. An attempt to reuse the syringe assembly by applying a force to the plunger rod 140 in the proximal direction causes a portion of the plunger rod 140 to separate at the frangible connection or point 143. The frangible connection or point 143 is designed so that the force holding exerted on the protrusion by the locking rib 123 while proximal force is being applied to the plunger rod 140 is greater than the force needed to break the plunger rod at the frangible point 143 and, therefore, the frangible point breaks or separates before the user is able to overcome the force exerted on the protrusion by the rib.

Figure 18:
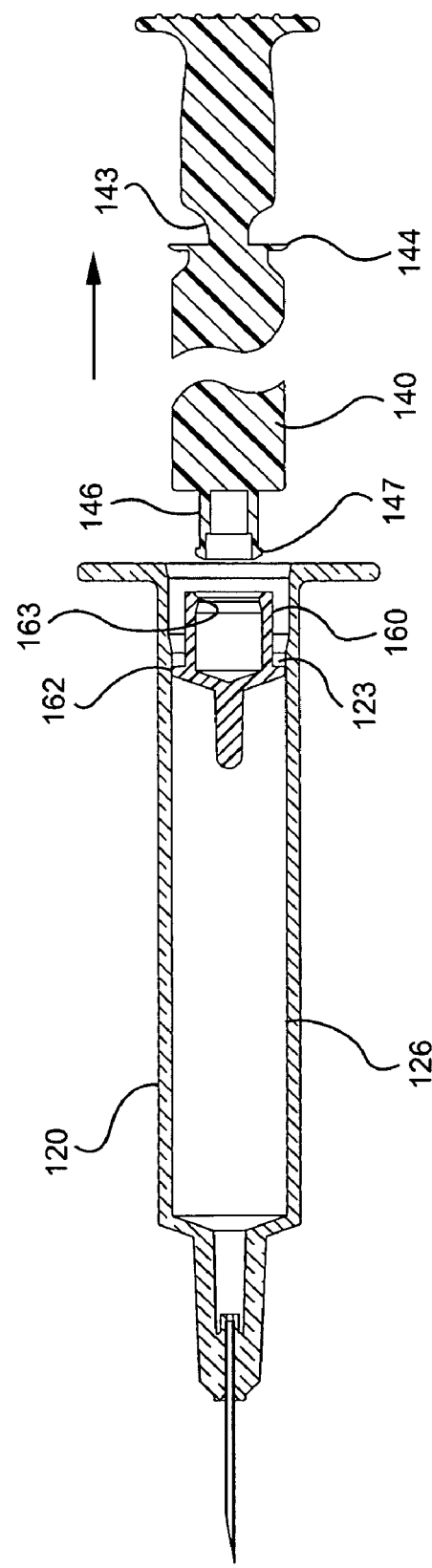
FIG. 18 is an illustration of FIG. 7 showing the plunger rod being moved in the proximal direction and the stopper disengaging from the plunger rod.

FIG. 18 shows the syringe assembly in a configuration in which the stopper 160 has separated from the stopper-engaging portion 146. According to one or more embodiments of the invention, the stopper 160 and stopper-engaging portion 146 disengage to prevent a user from disassembling the parts of the syringe assembly prior to use. As otherwise described in reference to FIG. 5, the peripheral edge 162 of the stopper 160 has a diameter greater than the diameter of the interior surface of the rib 123. Consistent with at least one embodiment of the invention, when a user applies a force to the plunger rod 140 in the proximal direction, the rib 123 locks the peripheral edge 162 of the stopper 160, and the rim 147 of the stopper-engaging portion 146 disconnects from the neck 163 of the stopper. The rib 123 exerts a greater force on the peripheral edge of the stopper than the force or friction exerted by the rim of the stopper-engaging portion of the plunger rod and neck portion of the stopper while proximal force is applied to the plunger rod.

Figure 19:
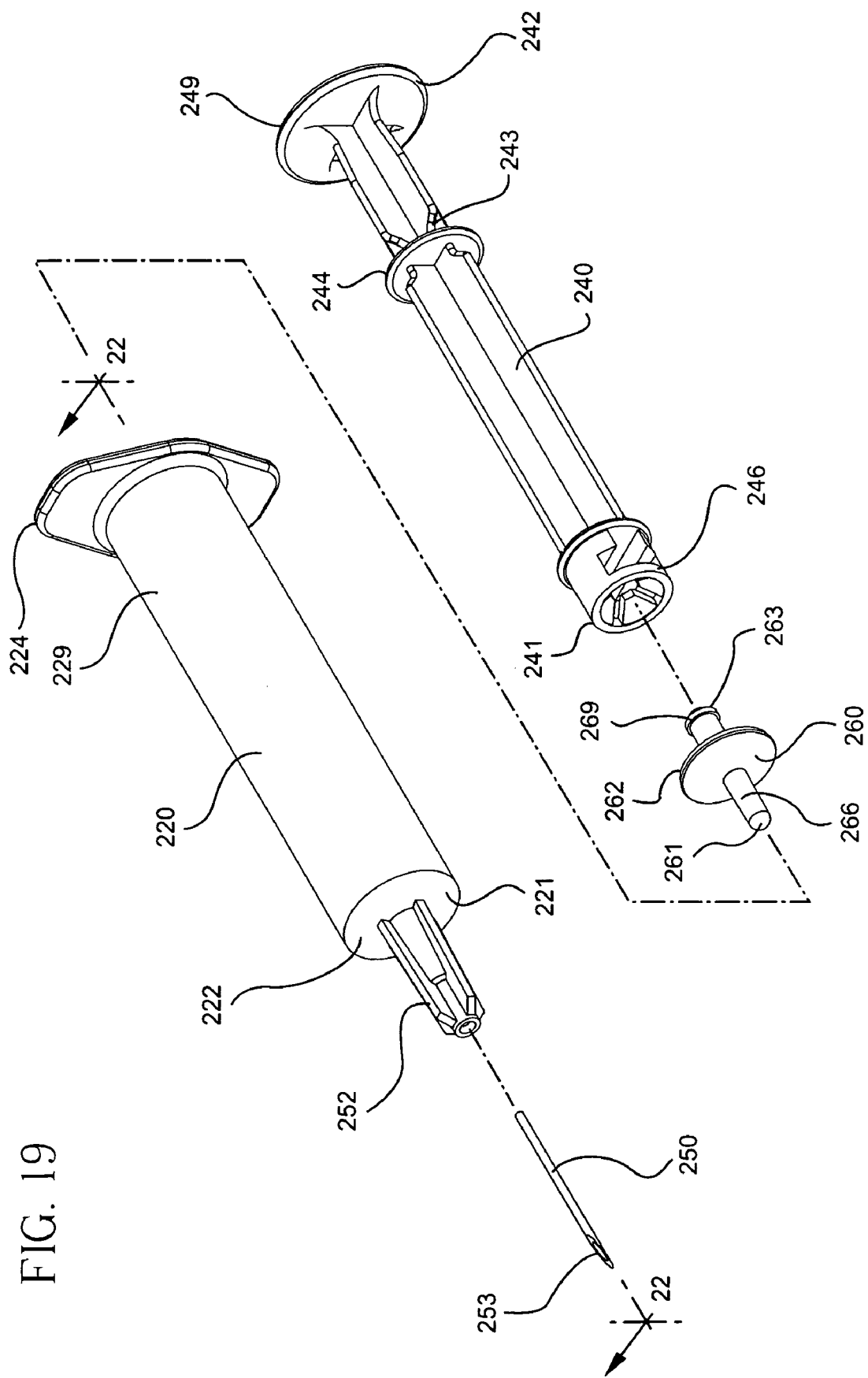
FIG. 19 a disassembled perspective view of a syringe assembly according to another embodiment of the invention.

FIG. 19 shows an example of a syringe assembly according to another embodiment of the present invention. In the embodiment shown in FIG. 19, the assembly includes a barrel 220, a plunger rod 240 and a stopper 260, arranged so that the proximal end of stopper 269 is attached to the distal end of the plunger rod 241. The stopper 260 then plunger rod 240 is inserted into the proximal end of the barrel 229. A flange 224 is attached at the proximal end 229 of the barrel 220. The barrel 220 further includes a needle cannula 250 having a lumen 253, attached to the opening in the distal wall 222 at the distal end 221 of the barrel 220. One or more embodiments also include an attachment hub 252 for attaching the needle cannula 250 to the distal wall 222. The assembly may also include a protective cap over the needle cannula (not shown).

Similar to the barrel illustrated previously in FIGS. 3 and 4, and as shown in FIG. 22, the barrel further include a rib 223, locking rib or other means for locking the plunger rod within the barrel, having an interior surface with a smaller diameter than the diameter of the interior surface of the barrel.

Figure 20:
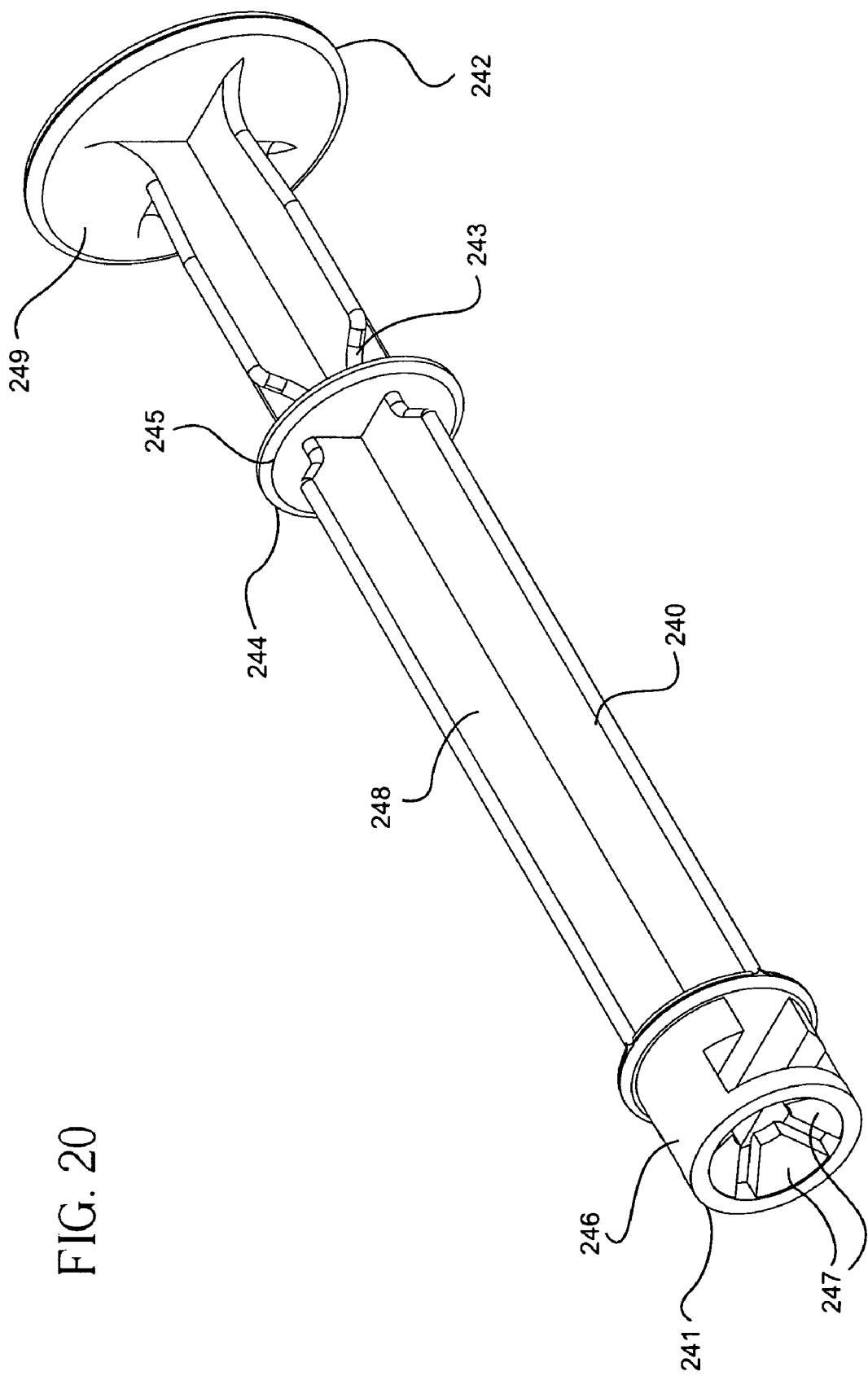
FIG. 20 is a perspective view of the plunger rod shown in FIG. 19.

Referring now to FIG. 20, a perspective view of a plunger rod 240 is shown as having a main body 248, a distal end 241 and a proximal end 249. The plunger rod 240 further includes a thumb press 242 at its proximal end and a stopper-engaging portion 246 at its distal end. Plunger rod 240 also includes a protrusion in the form of an annular protrusion 244 between the thumb press 242 and the main body 248. The protrusion 244 may include a tapered portion 245 to facilitate distal movement of the protrusion 244 past the rib 223 into the barrel 220. In some embodiments, the protrusion 244 has an outer diameter greater than the inner diameter of the barrel at the rib 223. In at least one embodiment, the configuration of the syringe assembly allows for the protrusion 244 to advance distally past the rib 223, to lock the plunger rod 240 in the barrel 220, when the user bottoms the syringe assembly (as more clearly shown in FIGS. 25-26 and discussed further below).

The plunger rod 240 shown further includes at least one frangible point 243. In the embodiment shown, the frangible point 243 of the plunger rod 240 is located between the protrusion 244 and the thumb press 242, but the frangible point could be in another location. A stopper-engaging portion 246 is included on the distal end 241 of the plunger rod 240. As shown, the stopper-engaging portion 246 also includes a plunger recess and a retainer 247. At least one embodiment of the invention includes a press-fit attachment or other suitable means for retaining the end of the stopper.

Figure 21:
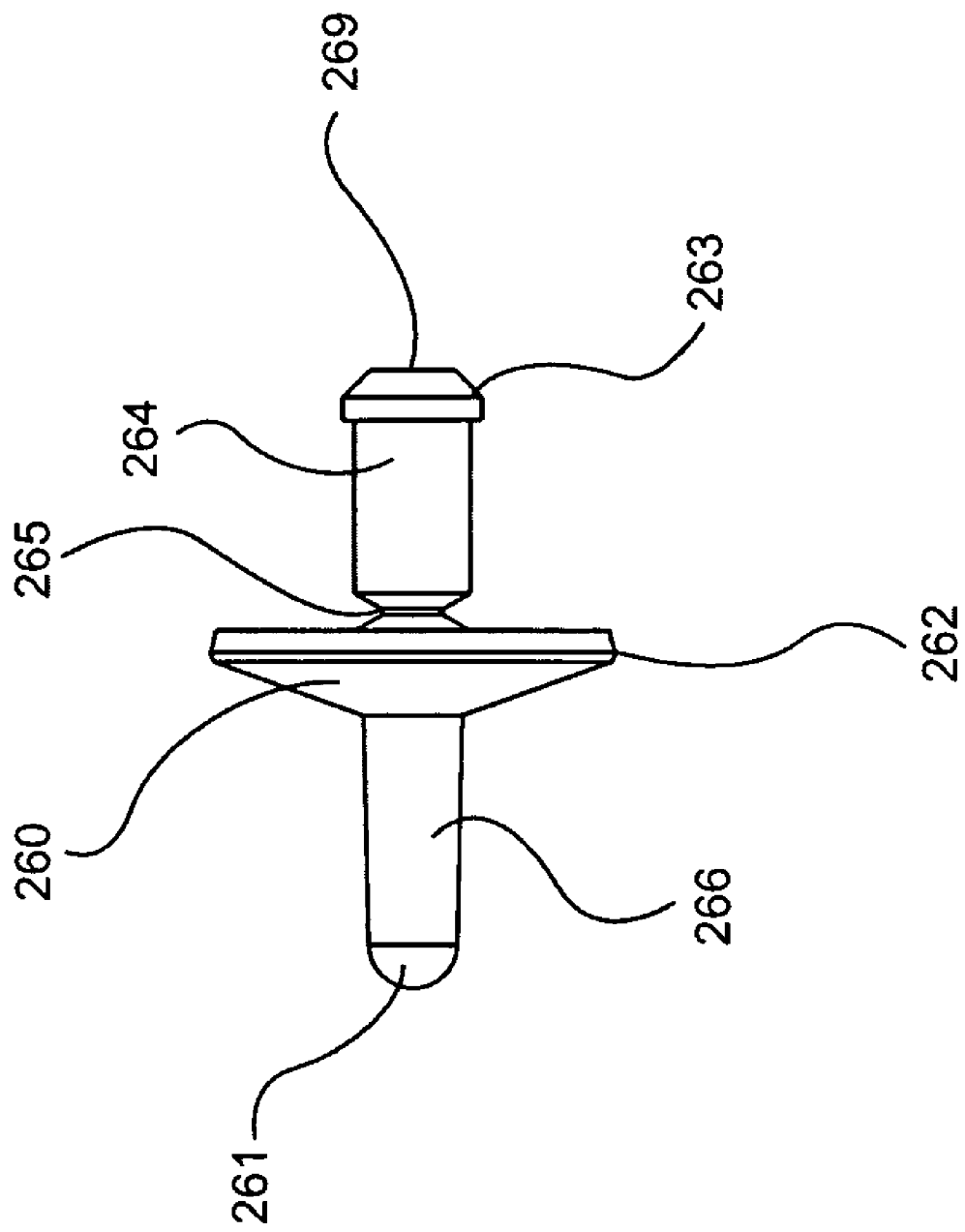
FIG. 21 is a side elevational view of the stopper shown in FIG. 19.

Referring now to FIG. 21, which shows an embodiment of the stopper 260 having a distal end 261 and a proximal end 269. According to at least one embodiment, the stopper 260 includes a peripheral edge 262 which forms a seal with the interior wall of the barrel 220 and has a diameter greater than the diameter of the interior surface of the barrel at the location of the rib 223 (as more clearly shown in FIGS. 22-24). As shown, an elongate tip 266 is provided at the distal end 261 of the stopper 260 to help expel the entire contents of the syringe. The stopper 220 can further include a stopper body 264 having a peripheral lip 263 at its proximal end 269, according to at least one embodiment of the invention. Further, the stopper 260 can include a stopper frangible connection 265 connecting the stopper body 264 to the stopper 260.

In this configuration, the stopper 260 and plunger rod 240 occupy the chamber of the barrel 220 and the stopper is bottomed against the distal wall of the barrel. Further, the peripheral edge 262 of the stopper 260 forms a seal with the interior surface of the barrel 220. The stopper 260 is connected to the stopper-engaging portion 246 of the plunger rod 240. As shown, the retainer 247 of the stopper-engaging portion 246 retains the peripheral lip 263 of the stopper 260.

Embodiments of the syringe assembly of FIGS. 19-27 can also include a visual marker 300, visual indicator 310 or both, as described with reference to FIGS. 13-16. In a specific embodiment, the barrel 220 of one or more embodiments can also include a visual marker aligned with the locking rib 223. In a more specific embodiment, the syringe assembly can include a visual indicator disposed on the stopper body 264.

According to one or more embodiments, there is a gap between the stopper 260 and the distal end of the main body 248 defining a pre-selected axial distance 232. In one or more embodiments, the distance between the protrusion 244 and the peripheral edge 262 of the stopper 260 defines a first distance, D1.

FIG. 23 illustrates the syringe assembly in use and specifically shows movement of the plunger rod during an aspiration or filling step according to one or more embodiments of the present invention. When the user applies a force to the plunger rod in the proximal direction, the plunger rod 240 and the stopper 260 move together in the proximal direction as indicated by the arrow, while the stopper-engaging portion 246 is connected to the stopper 260 by the rim 263. In this configuration, the gap defining the pre-selected axial distance 232 is maintained while the stopper 260 and plunger rod 240 move together in the proximal direction. The user applies proximal force to the plunger rod until a predetermined or desired amount of medicament is aspirated or drawn into the syringe. During the aspiration step, the plunger rod and the stopper body move in the proximal direction together to draw medication into the syringe, while maintaining the first distance D1.

FIG. 24 also shows the syringe assembly when distal force is applied to the plunger rod during an injection step according to at least one embodiment of the present invention. Application of a force in the distal direction closing the gap and moving the pre-selected axial distance 232 shown in FIG. 22, while the stopper 260 remains stationary. Consistent with at least one embodiment, once the stopper-engaging portion 246 has distally moved the pre-selected axial distance 232 and is in contact with stopper frangible connection 265, the stopper 260 and the plunger rod 240 begin to move in tandem in the distal direction.

When expelling the contents of the syringe, the plunger rod moves in a distal direction the length of the pre-selected axial distance 232 while the stopper body remains stationary. During and after the contents of the syringe have begun to be or have been fully expelled, the distance between the protrusion 244 and the peripheral edge 262 defines a second distance, D2, wherein D2 is the difference between the first distance, D1, and the gap defining a pre-selected axial distance 232.

In one embodiment, the user may inject a limited amount of the fluid aspirated or exert a limited force on the plunger rod in the distal direction to flush or expel some of the aspirated fluid, without locking the plunger rod, provided that the syringe assembly is not bottomed. However, as will be described further below, a user will typically expel substantially all of the contents of the syringe by bottoming the stopper on the distal wall of the barrel.

Referring now to FIG. 25, which illustrates the syringe assembly after the plunger rod 240 has been locked inside the barrel 220, the distal movement of the stopper-engaging portion 246 to the stopper frangible connection 265 of the stopper 260 (as also shown in FIG. 24) closes the gap defining the pre-selected axial distance and allows the protrusion 244 to advance past the rib 223, thereby locking the plunger rod 240 inside the barrel 220, preventing re-use of the syringe assembly.

Referring now to FIG. 26, the syringe assembly is shown in a configuration in which a user attempts to reuse the syringe assembly after the plunger rod 240 is locked inside the barrel 220 by applying a force to the plunger rod 240 in the proximal direction. Application of sufficient proximal force to the plunger rod causing a portion of the plunger rod 240 to separate at the frangible connection or point 243, as the holding force of the protrusion 244 and the rib exceeds the breaking force of the frangible point or connection.

FIG. 27 shows the syringe assembly in a configuration after which proximal force has been applied to the plunger rod and the stopper has moved to the proximal end of the barrel. As shown in FIG. 27, the stopper 260 has separated from the stopper-engaging portion 246 of the plunger rod. The stopper frangible connection 265 breaks to prevent a user from disassembling the parts of the syringe assembly. As otherwise described herein, the peripheral edge of the stopper 262 has an outer diameter greater than the inner diameter of the interior surface of the barrel at the location of the rib 223. Consistent with at least one embodiment of the invention, when a user applies a force to the plunger rod 240 in the proximal direction, the rib 223 of the barrel 220 locks the peripheral edge 262 of the stopper 260, and the stopper frangible connection 265 breaks, separating the stopper body 264 from the stopper 260. Without being limited by theory, it is believed that the force required to break the frangible connection is less than the force exerted on the peripheral edge of the stopper.

According to one or more embodiments, the syringe barrel may include identifying information on the syringe assembly. Such information can include, but is not limited to one or more of identifying information regarding the contents of the syringe assembly or information regarding the intended recipient.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
   a barrel including a cylindrical sidewall having an interior surface defining a chamber for retaining fluid, an open proximal end and a distal end including a distal wall having an opening therethrough in fluid communication with said chamber, said sidewall including a rib adjacent said proximal end and a diameter transition region having an axial length extending from the rib towards said proximal end such that the diameter of the barrel increases along the transition region from the rib towards the proximal end;
   an elongate plunger rod including a proximal end, a distal end, and a main body extending between the proximal and distal end, the plunger rod being distally and proximally movable within said chamber, the proximal end including a thumb press, the distal end including a stopper-engaging portion, the plunger rod further including a protrusion between the thumb press and the main body, the protrusion having a diameter greater than the diameter of the barrel at the rib and the plunger rod further including at least one frangible portion;
   a stopper having a proximal end, a distal end and a peripheral edge that forms a seal with the interior surface of the barrel having a diameter greater than the diameter of the barrel at the rib, the stopper attached to the stopper-engaging portion of the plunger rod, the stopper being distally and proximally movable relative to the stopper-engaging portion for a pre-selected axial distance such that when the distal end of the stopper is in contact with the distal wall of the barrel, the protrusion is permitted to advance distally past the rib in the barrel and lock the plunger rod in the barrel to prevent reuse of the syringe assembly, the stopper-engaging portion comprising a visual indicator that is fully visible before an initial distally directed force is applied to the plunger rod.

2. The syringe assembly of claim 1, wherein the stopper further comprises a stopper boss at the proximal end of the stopper and a frangible connection connecting said stopper to the plunger rod.

3. The syringe assembly of claim 2, further comprising a peripheral lip at a proximal end of the stopper boss.

4. The syringe assembly of claim 2, wherein the stopper-engaging portion of the plunger rod further comprises a retainer to retain the peripheral lip of the stopper.

5. The syringe assembly of claim 1, wherein the protrusion is tapered to facilitate distal movement.

6. The syringe assembly of claim 1, wherein the stopper-engaging portion of the plunger rod is connected to the stopper such that upon application of an initial proximally directed force to the plunger rod, while holding the barrel, causes the plunger rod to move the length of the axial distance in a proximal direction within the barrel, while the stopper remains stationary.

7. The syringe assembly of claim 6, wherein the stopper-engaging portion of the plunger rod is connected to the stopper such that upon application of a continuous proximally directed force to the plunger rod, while holding the barrel, causes the stopper and the plunger rod to move together in a proximal direction within the barrel.

8. The syringe assembly of claim 7, wherein the stopper-engaging portion of the plunger rod is connected to the stopper such that application of an initial distally directed force to the plunger rod after application of a proximally directed force to the plunger rod, while holding the barrel, causes the stopper to remain stationary and the plunger to move the length of the axial distance in the distal direction within the barrel.

9. The syringe assembly of claim 8, wherein the stopper-engaging portion of the plunger rod is connected to the stopper such that application of a continuous distally directed force to the plunger rod causes the stopper and plunger rod to move together in the distal direction within the barrel until the stopper reaches the distal end of the barrel, thereby allowing the protrusion to advance distally past the rib in the barrel and lock the plunger rod in the barrel to prevent reuse of the syringe assembly.

10. The syringe assembly of claim 1, wherein application of a proximally directed force to the plunger, after the protrusion has advanced distally past the rib, causes the at least one frangible portion of the plunger rod to break.

11. The syringe assembly of claim 1, wherein application of a continuous proximally directed force on the plunger rod causes the stopper-engaging portion to disengage from the stopper.

12. The syringe assembly of claim 3, wherein a continuous proximally directed force on the plunger rod causes the frangible connection to break.

13. The syringe assembly of claim 1, wherein the proximal end of the barrel further comprising a flange.

14. The syringe assembly of claim 1, wherein the barrel further comprising a needle cannula attached to the opening of the barrel.

15. The syringe assembly of claim 10, further comprising a second frangible point.

16. The syringe assembly of claim 1, wherein the visual indicator is not visible when the protrusion is permitted to advance distally past the rib in the barrel and lock the plunger rod in the barrel to prevent reuse of the syringe assembly.

17. The syringe assembly of claim 1, further comprising a visual marker disposed on the barrel and aligned with the rib such that when the distal end of the stopper is in contact with the distal wall of the barrel, the protrusion is permitted to advance distally past the visual marker on the barrel to indicate the plunger rod is locked in the barrel.

18. A syringe assembly comprising:
   a barrel including a cylindrical sidewall having an interior surface defining a chamber for retaining fluid, an open proximal end and a distal end including a distal wall having an opening therethrough in fluid communication with said chamber, the chamber further having a first inner diameter, a locking rib adjacent to the open proximal end having a second inner diameter, wherein the second inner diameter is less than the first inner diameter, an increased diameter region located proximally from the locking rib having a third inner diameter greater than the first and second inner diameters, and a diameter transition region extending between the locking rib and the increased diameter region;

an elongate plunger rod having a proximal end, a distal end, a stopper-engaging portion located at the distal end of the plunger rod, a thumb press at the proximal end of the plunger rod, a main body portion extending between the distal and proximal ends of the plunger rod, an annular protrusion extending radially from the plunger rod having an outer diameter greater than the second inner diameter and the plunger rod further including at least one frangible portion;

a stopper having a proximal end and a distal, the stopper attached to the stopper-engaging portion of the plunger rod, the stopper being distally and proximally movable a pre-selected axial distance relative to the stopper-engaging portion, such that when the distal end of the stopper is in contact with the distal wall of the barrel, the annular protrusion is permitted to advance distally past the locking rib in the barrel and lock the plunger rod in the barrel to prevent reuse of the syringe assembly; and a use detection system including a visual display disposed on the stopper-engaging portion of the plunger rod, the visual display being fully visible before an initial distally directed force is applied to the plunger rod.

19. The syringe assembly of claim 18, wherein the stopper further comprises a stopper boss at the proximal end of the stopper and a frangible connection connecting said stopper to the plunger rod.

20. The syringe assembly of claim 19, further comprising a peripheral lip at a proximal end of the stopper boss.

21. The syringe assembly of claim 20, wherein the stopper-engaging portion of the plunger rod further comprises a retainer to retain the peripheral lip of the stopper.

22. The syringe assembly of claim 18, wherein the annular protrusion is tapered to facilitate distal movement past the locking rib.

23. The syringe assembly of claim 18, wherein the stopper-engaging portion of the plunger rod is connected to the stopper such that application of an initial proximally directed force to the plunger rod, while holding the barrel, causes the plunger rod to move the length of the axial distance in a proximal direction within the barrel, while the stopper remains stationary.

24. The syringe assembly of claim 23, wherein the stopper-engaging portion of the plunger rod is connected to the stopper such that application of a continuous proximally directed force to the plunger rod, while holding the barrel, causes the stopper and the plunger rod to move together in a proximal direction within the barrel.

25. The syringe assembly of claim 24, wherein the stopper-engaging portion of the plunger rod is connected to the stopper such that application of an initial distally directed force to the plunger rod after application of a proximally directed force to the plunger rod, while holding the barrel, causes the stopper to remain stationary and the plunger to move the length of the axial distance in the distal direction within the barrel.

26. The syringe assembly of claim 25, wherein the stopper-engaging portion of the plunger rod is connected to the stopper such that application of a continuous distally directed force to the plunger rod causes the stopper and plunger rod to move together in the distal direction within the barrel until the stopper reaches the distal end of the barrel, thereby allowing the annular protrusion to advance distally past the locking rib in the barrel and lock the plunger rod in the barrel to prevent reuse of the syringe assembly.

27. The syringe assembly of claim 18, wherein application of a proximally directed force to the plunger, after the protrusion has advanced distally past the rib, causes the at least one frangible portion of the plunger rod to break.

28. The syringe assembly of claim 27, wherein the stopper has a diameter greater than the second inner diameter.

29. The syringe assembly of claim 28, wherein, upon application of a continuous proximally directed force on the plunger rod, the locking rib prevents proximal movement of the stopper and causes the stopper-engaging portion to disengage from the stopper.

30. The syringe assembly of claim 21, wherein the stopper has a diameter greater than the second inner diameter.

31. The syringe assembly of claim 30, wherein, upon application of a continuous proximally directed force on the plunger rod, the locking rib prevents proximal movement of the stopper and causes the frangible connection to break.

32. The syringe assembly of claim 18, wherein the proximal end of the barrel further comprising a flange.

33. The syringe assembly of claim 18, wherein the barrel further comprising a needle cannula attached to the opening of the barrel.

34. The syringe assembly of claim 27, further comprising a second frangible point.

35. The syringe assembly of claim 18, wherein the visual indicator is not visible when the protrusion is permitted to advance distally past the rib in the barrel and lock the plunger rod in the barrel to prevent reuse of the syringe assembly.

36. The syringe assembly of claim 18, further comprising a visual marker disposed on the barrel and aligned with the locking rib such that when the distal end of the stopper is in contact with the distal wall of the barrel, the position of the protrusion moves from being positioned proximally adjacent to the locking rib to distally adjacent to the visual marker to indicate the plunger rod is locked in the barrel.

37. A syringe assembly comprising:
a barrel including a cylindrical sidewall having an interior surface defining a chamber for retaining fluid, an open proximal end and a distal end including a distal wall having an opening therethrough in fluid communication with said chamber;

an elongate plunger rod having a proximal end, a distal end, a stopper-engaging portion located at the distal end of the plunger rod, a thumb press at the proximal end of the plunger rod, and a main body portion extending between the distal and proximal ends of the plunger rod;

a stopper having a proximal end and a distal end, the stopper attached to the stopper-engaging portion of the plunger rod, the stopper being distally and proximally movable relative to the stopper-engaging portion;

means for locking the plunger rod in the barrel to prevent reuse of the syringe assembly when the distal end of the stopper is in contact with the distal wall of the barrel and distal force is applied to the thumb press;

means for separating at least a portion of the plunger rod from the main body upon application of sufficient proximal force to the plunger rod;

means for separating the stopper from the stopper-engaging portion of the plunger rod upon application of sufficient proximal force on the plunger rod; and indicator means for indicating that the plunger rod is locked in the barrel.

38. The syringe assembly of claim 37, wherein the means for separating at least a portion of the plunger rod is located adjacent the proximal end of the plunger rod and is operable to break a portion of the plunger rod when the plunger rod is locked in the barrel.

39. The syringe assembly of claim 37, wherein the stopper-engaging portion of the plunger rod is connected to the stopper such that application of an initial proximally directed force to the plunger rod, while holding the barrel, causes the plunger rod to move in a proximal direction within the barrel, while the stopper remains stationary.

40. The syringe assembly of claim 39, wherein the stopper-engaging portion of the plunger rod is connected to the stopper such that application of a continuous proximally directed force to the plunger rod, while holding the barrel, causes the stopper and the plunger rod to move together in a proximal direction within the barrel.

41. The syringe assembly of claim 40, wherein the stopper-engaging portion of the plunger rod is connected to the stopper such that application of an initial distally directed force to the plunger rod after application of a proximally directed force to the plunger rod, while holding the barrel, causes the stopper to remain stationary and the plunger to move in the distal direction within the barrel.

42. The syringe assembly of claim 41, wherein the stopper-engaging portion of the plunger rod is connected to the stopper such that application of a continuous distally directed force to the plunger rod causes the stopper and plunger rod to move together in the distal direction within the barrel until the stopper reaches the distal end of the barrel, thereby engaging the means for locking the plunger rod to prevent reuse of the syringe assembly.

* * * * *